(12) United States Patent
Itoh et al.

(10) Patent No.: US 6,797,695 B1
(45) Date of Patent: Sep. 28, 2004

(54) HUMAN FGF-20 GENE AND GENE EXPRESSION PRODUCTS

(75) Inventors: Nobuyuki Itoh, Kyoto (JP); Michael Kavanaugh, Mill Valley, CA (US)

(73) Assignees: Kyoto University, Kyoto (JP); Chiron Corporation, Emeryville, CA (US)

( * ) Notice: Subject to any disclaimer, the term of this patent is extended or adjusted under 35 U.S.C. 154(b) by 402 days.

(21) Appl. No.: 09/692,945

(22) Filed: Oct. 20, 2000

Related U.S. Application Data

(60) Provisional application No. 60/187,856, filed on Mar. 8, 2000, and provisional application No. 60/161,162, filed on Oct. 22, 1999.

(51) Int. Cl.[7] .......................... A61K 38/18; C07K 14/50
(52) U.S. Cl. ......................................... 514/12; 530/350
(58) Field of Search ............................. 514/12; 535/350

(56) References Cited

U.S. PATENT DOCUMENTS

| | | | |
|---|---|---|---|
| 5,766,883 A | 6/1998 | Ballance et al. | 435/69.7 |
| 5,876,969 A | 3/1999 | Fleer et al. | 435/69.7 |
| 6,110,893 A | 8/2000 | Hu et al. | 514/12 |
| 2002/0058036 A1 | 5/2002 | Jeffers et al. | 424/145.1 |

FOREIGN PATENT DOCUMENTS

| | | |
|---|---|---|
| WO | WO 97/24445 | 7/1997 |
| WO | WO 00/54813 | 9/2000 |
| WO | WO 00/60085 | 10/2000 |
| WO | WO 01/07595 | 2/2001 |
| WO | WO 01/18209 | 3/2001 |

OTHER PUBLICATIONS

Xie et al. FGF–19, a novel fibroblast growth factor with unique specificity for FGFR4. Cytokine. 1999 Oct.; 11(10):729–35.
Szebenyi et al. Fibroblast growth factors as multifunctional signaling factors. Int Rev Cytol. 1999; 185:45–106.
Aaronson et al., "Keratinocyte Growth Factor: A Fibroblast Growth Factor Family Member With Unusual Target Cell Specificity," *Annals of the New York Academy of Sciences* 638:62–77, 1991.
Akashi, "Synonymous Codon Usage in *Drosophila Melanogaster*: Natural Selection and Translational Accuracy," *Genetics* 136(3):927–935, Mar. 1994.
Baird and Klagsbrun, "The Fibroblast Growth Factor Family," *Cancer Cells* 3(6):239–243, Jun. 1991.
Baloh et al., "Artemin a Novel Member of the GDNF Ligand Family, Supports Peripheral and Central Neurons and Signals through The GFRα 3–RET Receptor Complex," *Neuron.* 21:1291–1302, Dec. 1998.
Belluardo et al., "Comparative Localization of Fibroblast Growth Factor Receptor–1, 2, and –3 mRNAs in the Rat Brain: In Situ Hybridization Analysis," *J. Comparative Neurology* 379:226–246, 1997.

Blunt et al., "Overlapping Expression and Redundant Activation of Mesenchymal Fibroblast Growth Factor (FGF) Receptors by Alternatively Spliced FGF–8 Ligands," *The Journal of Biological Chemisty* 272(6):3733–3738, Feb. 7, 1997.
Bracci–Laudiero et al., "Increased Levels of NGF in Sera of Systemic Lupus Erthematosus Patients," *NeuroReport* 4(5):563–565, May 1993.
Burgess and Maciag, "The Heparin–Binding (Fibroblast) Growth Factor Family or Proteins," *Annu. Rev. Biochem* 58:575–606, 1989.
Colvin et al., "Skeletal Overgrowth and Deafness in Mice Lacking Fibroblast Growth Factor Receptor 3," *Nature Genetics* 12(4):390–397, Apr. 1996.
Coulier et al., "The FGF6 Gene Within the FGF Multigene Family," *Annals of the New York Academy of Sciences* 638:53–61, 1991.
Crossley and Martin, "The Mouse Fgf8 Gene Encodes a Family of Polypeptides and Is Expressed In Regions That Direct Outgrowth and Patterning in the Developing Embryo," *Development* 121:439–451, 1995.
Davis et al., "Enzyme–Polyethylene Glycol Adducts: Modified Enzymes with Unique Properties," *Enzyme Engineering* 4:169–173.
Dazert et al., "Focal Delivery of Fibroblast Growth Factor–1 by Transfected Cells Induces Spiral Ganglion Neurite Targeting In Vitro," *J. of Cellular Physiology* 177:123–129, 1998.
Dickson et al., "Expression Processing, and Properties of int–2," *Annals of the New York Academy of Sciences* 638:18–26, 1991.
Dunnett and Björkland, "Propsects for New Restorative and Neuroprotective Treatments in Parkinson's Disease," *Nature* 399(supplemental:A32–A39, Jun. 24, 1999.
Elde et al., "Prominent Expression of Acidic Fibroblast Growth Factor in Motor and Sensory Neurons," *Neuron* 7(3):349–364, Sep. 1991.
Emoto et al., "Basic Fibroblast Growth Factor (FGF) in the Central Nervous System: Identification of Specific Loci of Basic FGF Expression in the Rat Brain," *Growth Factors* 2:21–29, 1989.

(List continued on next page.)

*Primary Examiner*—David S. Romeo
(74) *Attorney, Agent, or Firm*—Jane E. R. Potter; Lisa E. Alexander; Robert P. Blackburn

(57) ABSTRACT

This invention relates to human fibroblast growth factor (hFGF-20), and to variants thereof and to polynucleotides encoding FGF-20. The invention also relates to diagnostic and therapeutic agents related to the polynucleotides and proteins, including probes and antibodies, to methods of treating neuronal degenerative disease such as Parkinson's disease and to methods of treating disorders of the cochlea including those causing hearing loss. The invention also relates to rat fibroblast growth factor (rFGF-20), and to variants thereof and polynucleotides encoding rFGF-20.

4 Claims, 17 Drawing Sheets

OTHER PUBLICATIONS

Emfors et al., "Identification of Cells in Rat Brain and Peripheral Tissues Expressing mRNA for Members of the Nerve Growth Factor Family," *Neuron* 5(4):511–526, Oct. 1990.

Fallon and Loughlin, *The Rat Nervous System*, 2nd ed., Academic Press, California, 1995 Chapter 12, "Substantia Nigra," pp. 215–237.

Friden et al., "Blood–Brain Barrier Penetration and in Vivo Activity of an NGF Conjugate," *Science* 259:373–377, Jan. 15, 1993.

Gemel et al., "Short Communication: Structure and Sequence of Human FGF8," *Genomics* 35(1):253–257, Jul. 1, 1996.

Ghosh et al., "Molecular Cloning and Characterization of Human FGF8 Alternative Messenger RNA Forms," *Cell Growth & Differentiation* 7(10):1425–1434, Oct. 1996.

Goldfarb et al., "Expression and Possible Functions of the FGF–5 Gene," *Annals of the New York Academy of Sciences* 638:38–52, 1991.

Gospodarowicz and Cheng, "Heparin Protects Basic and Acidic FGF From Inactivation," *J. of Cellular Physiology* 128:475–484, 1986.

Gospodarowicz, "Isolation and Characterization of Acidic and Basic Fibroblast Growth Factor," *Methods in Enzymology* 147(B):106–119, 1987.

Haub et al., "Expression of the Murine Fibroblast Growth Factor 5 Gene in the Adult Central Nervous System," *Proc. Natl. Acad. Sci. USA* 87:8022–8026, Oct. 1990.

Hoshikawa et al., "Structure and Expression of a Novel Fibroblast Growth Factor, FGF–17, Preferentially Expressed in the Embryonic Brain," *Biochemical and Biophysical Research Communications* 244(1):187–191, Mar. 6, 1988.

Hyman et al., "BDNF is a Neurotrophic Factor for Dopaminergic Neurons of the Substantia Nigra," *Nature* 350(6315):230–232, Mar. 21, 1991.

Hyman et al., "Overlapping and Distinct Actions of Neurotrophins BDNF, NT–3 and NT–4/5 on Cultured Dopaminergic and GABAergic Neurons of the Ventral Mesencephalon," *J. of Neuroscience* 14(1):335–347, Jan. 1994.

Laudiero et al., "Multiple Sclerosis Patients Expresss Increased Levels of β–Nerve Growth Factor in Cerebrospinal Fluid," *Neuroscience Letters* 147:9–12, 1992.

Lin et al., "GDNF: A Glial Cell Line—Derived Neurotrophic Factor for Midbrain Dopaminergic Neurons," *Science* 260:1130–1132, May 12, 1993.

Lloyd and Sharp, "Evolution of Codon Usage Patterns: The Extent and Nature of Divergence Between *Candida Albicans* and *Saccharomyces Cerevisiae*," *Nucleic Acids Research* 20(20):5289–5295, 1992.

Lopez et al., "Basci Fibroblast Growth Factor in a Porcine Model of Chronic Myocardial Ischemia: A Comparison of Angiographic, Echocardiographic and Coronary Flow Parameters," *The J. of Pharmacology and Experimental Therapeutics* 282(1):385–390, Jul. 1997.

Malumbres et al., "Codon Preference in Corynebacteria," *Gene* 134:15–24, 1993.

McQueen et al., "Non–Insulin–Dependent Diabetic Microangiopathy in the Inner Ear;" *The J. of Laryngology and Otology* 113:13–18, Jan. 1999.

McWhirter et al., "A Novel Fibroblast Growth Factor Gene Expressed in the Developing Nervous System in a Downstream Target of the Chimeric Homeodomain Oncoprotein E2A–Pbx1," *Development* 124:3221–3232, 1997.

Millbrandt et al., "Persephin, a Novel Neurotrophic Factor Related to GDNF and Neurturin," *Neuron* 20(2):245–253, Feb. 1998.

Miyake et al., "Structure and Expression of a Novel Member, FGF–16, of the Fibroblast Growth Factor Family," *Biochemical and Biophysical Reseach Communications* 243(1):148–152, Feb. 4, 1998.

Miyamoto et al., "Molecular Cloning of a Novel Cytokine cDNA Encoding in Ninth Member of the Fibroblast Growth Factor Family, Which Has a Unique Secretion Property," *Molecular and Cellular Biology* 13(7):4251–4259, Jul. 1993.

Nielsen et al., "Identification of Prokaryotic and Eukaryotic Signal Peptides and Prediction of Their Cleavage Sites," *Protein Engineering* 10:1–6, 1997.

Nishimura et al., "Structure and Expression of a Novel Human FGF, FGF–19, Expressed In the Fetal Brain," *Biochimica et Biophysica Acta* 1444(1):148–151, 1999.

Ohbayashi et al., "Structure and Expression of the mRNA Encoding a Novel Fibroblast Growth Factor, FGF–18," *The J. of Biological Chemistry* 273(29):18161–18164, Jul. 17, 1998.

Ohuchi et al., "The Mesenchymal Factor, FGF10, Initiates and Maintains the Outgrowth of the Chick Limb Bud Through Interaction With FGF8, An Apical Ectodermal Factor," *Development* 124:2235–2244, 1997.

Otten and Gadient, "Neurotrophins and Cytokines—Intermediates Between the Immune and Nervous Systems," *Int. J. Devl. Neuroscience* 13(3/4):147–151, 1995.

Ozawa et al., "Expression of the Fibroblast Growth Factor Family and Their Receptor Family Genes During Mouse Brain Development," *Molecular Brain Research* 41:279–288, 1996.

Pickles and van Heumen, "The Expression of Messenger RNAs Coding for Growth Factors, Their Receptors, and eph–Class Receptor Tyrosine Kinases in Normal and Ototoxically Damaged Chick Cochleae," *Development Neurowscience* 19:476–487, 1997.

Pochon et al., "Neuronal GDNF Expression in the Adult Ray Nervous System Identified by In Situ Hybridization," *European J. of Neuroscience* 9(3):463–471, Mar. 1997.

Reich–Slotky et al., "Chimeric Molecules Between Keratinocyte Growth Factor and Basic Fibroblast Growth Factor Define Domains That Confer Receptor Binding Specificities," *The J. of Biological Chemistry* 270(50):29813–29818, Dec. 15, 1995.

Schneider and Benner, "Building Blocks for Oligonucleotide Analogs with Dimethylene–Sulfide, Sulfoxide, and –Sulfone Groups Replacing Phosphodiester Linkages," *Tetrahedron Letters* 31(3):335–338, 1990.

Scully and Otten, "NGF: Not Just for Neurons," *Cell Biology International* (*Special Issue*) 19(5):459–469, 1995.

Smallwood et al., "Fibroblast Growth Factor (FGF) Homologous Factors: New Members of the FGF Family Implicated in Nervous System Development," *Proc. Natl. Acad. Sci. USA* 93:9850–9857, Sep. 1996.

Tanaka et al, "Human Androgen–Induced Growth Factor in Prostate and Breast Cancer Cells: Its Molecular Cloning and Growth Properties," *FEBS Letters* 363(3):226–230, 1995.

Tanaka et al., "Cloning and Characterization of An Androgen–Induced Growth Factor Essential for the Androgen–Dependent Growth of Mouse Mammary Carcinoma Cells," *Proc. Natl. Acad. Sci. USA* 89:8928–8932, Oct. 1992.

Uhlmann and Peyman, "Antisense Oligonucleotides: A New Therapeutic Principle," *Chemical Reviews* 90(4):544–548, Jun. 1990.

Walicke, "Basic and Acidic Fibroblast Growth Factors Have Trophic Effects on Neurons from Multiple CNS Regions," *J. of Neuroscience* 8(7):2618–2627, Jul. 1988.

West and Iglewski, "Codon Usage in *Pseudomonas Aeruginosa,*" *Nucleic Acid Research* 16(19):9323–9335, 1988.

Wilke et al., "Expression of Fibroblast Growth Factor Receptors (FGFR1, FGFR2, FGFR3) in the Developing Head and Face," *Developmental Dynamics* 210:41–52, 1997.

Woodward et al., "Nuclear and Cytoplasmic Localization of Basic Fibroblast Growth Factor in Astrocytes and CA2 Hippocampal Neurons," *J. of Neuroscience* 12(1):142–152, Jan. 1992.

Yamamoto et al., "Structure and expression of a novel isoform of mouse FGF homologous factor (FHF)–4," *Biochimica et Biophysica Acta* 1398:38–41, 1998.

Yamasaki et al., "Structure and Expression of the Rat mRNA Encoding a Novel Member of the Fibroblast Growth Factor Family," *The J. of Biological Chemistry* 271(27):15918–15921, Jul. 5, 1996.

Yoshida et al., "Characterization of the hst–1 Gene and Its Product," *Annals of the New Academy of Sciences* 638:27–37, 1991.

Zheng et al., "Induction of Cell Proliferation by Fibroblast and Insulin–Like Growth Factors in Pure Rat Inner Ear Epithelial Cell Cultures," *The J. of Neuroscience* 17(1):216–226, Jan. 1, 1997.

Genbank database, Accession No. AB020858, May 21, 1999.

Kirikoshi et al., "Molecular Cloning and Characterization of Human FGF–20 on Chromosome 8p21.3–p22," *Biochemical and Biophysical Research Communications* 274(2):337–343, Aug. 2, 2000.

Koga et al., "Characterization of a Novel Member of the FGF Family, XFGF–20, in *Xenopus laevis,*" *Biochemical and Biophysical Research Communications* 261(3):756–765, Aug. 11, 1999.

Ohmachi et al., "FGF–20, a Novel Neurotrophic Factor, Preferentially Expressed in the Substantia Nigra Pars Compacta of Rat Brain," *Biochemical and Biophysical Research Communications* 277(2):355–360, Oct. 22, 2000.

```
rat FGF-9    MAPLGEVGSYF-GVCD-AVPFGNVPVL--PVDSPVLLSDHLGQSEAGGLPRGPAVTDLDHL  57
             ****  *****    *  ***    *    ***  *        **  *    ***
rat FGF-20   MAPLTEVGAFLGGLEGLGQQVGSHFLLPPAGERPPLLGERRGALE-RGARGGPGSVELAHL  60
                  *  *                  *              *    *     *  ****
rat FGF-16        MAEVGGVFASLDWDLQGFSSSLGNVPLADSPGFLNERLGQIE--GKLQRGSPTDFAHL  56

KGILRRRQLYCRTGFMLEIFPNGTIQGTRKDHSRFGILEFISIAVGLVSIRGVDSGLYLG  117
************************************** ***  *************
HGILRRRQLYCRTGFMLQILPDGSVQGTRQDHSLFGILEFISVAVGLVSIRGVDSGLYLG  120
*  ******************     *  ** **  *****  *  **  ********
KGILRRRQLYCRTGFHLEIFPNGTVHGTRHDHSRFGILEFISLAVGLISIRGVDSGLYLG  116

MNEKGELYGSEKLTQECVFREQFEENWYNTYSSNLYKHVDTGRRYYVALNKDGTPREGTR  177
*  *****  ****  *  ***  ******* ***    **** **** ********
MNGKGELYGSEKLTSFCIFREQFEENWYNTYSSNIYKHGDTGRRYFVALNKDGTPRDGAR  180
*  ***     ***    ****************  ***   *  *********    *
MNERGELFGSKKLTRECVFREQFEENWYNTYASTLYKHSDSERQYYVALNKDGSPREGYR  176

TKRHQKFTHFLPRPVDPDKVPELYKDILSQS      208  SEQ ID NO:16
*  ******************     *    ****
SKRHQKFTHFLPRPVDPERVPELYKDLLVYTG     212  SEQ ID NO:2
*  *******************  *  *
TKRHQKFTHFLPRPVDPSKLPSMSRDLFRYR      207  SEQ ID NO:17
```

SEQ ID NO:1

Rat FGF-20 DNA

Translation start and stop codons indicated in bold, underlined type.

```
CCTTCCATGGCTCCCTTGACCGAAGTCGGTGCCTTCTTGGGCGGCCTGGAGGGCTTGGGCCAGCAGGTGGGG
TCGCACTTCTTGCTGCCTCCTGCAGGGGAGCGACCGCCGCTGCTAGGGGAGCGGCGGGGCGCGTTGGAGCGG
GGCGCCCGCGGCGGGCCGGGTTCCGTGGAGCTGGCGCACCTGCACGGCATCCTGCGCCGCCGGCAGCTCTAC
TGCCGCACCGGCTTCCACCTGCAGATCCTGCCCGACGGCAGTGTGCAGGGCACCCGGCAGGATCACAGCGTC
TTCGGTATCCTGGAATTCATCAGTGTGGCGGTGGGGCTGGTCAGTATCAGAGGTGTGGACAGCGGCCTGTAC
CTTGGCATGAATGGCAAAGGAGAGCTTTATGGCTCAGAGAAATTGACTTCTGAATGCATCTTCAGGGAACAA
TTTGAAGAGAACTGGTATAATACCTATTCATCCAACATATACAAACACGGAGACACAGGTCGCAGGTATTTT
GTAGCACTTAACAAAGACGGGACTCCAAGGGACGGTGCCAGGTCCAAAAGACACCAAAAGTTTACCCATTTT
TTACCCAGACCAGTGGACCCAGAGAGAGTCCCAGAGTTATACAAAGACCTACTGGTGTACACTGGATGAACC
```

Figure 7

SEQ ID NO:2

Amino acid sequence of rat FGF-20

MAPLTEVGAFLGGLEGLGQQVGSHFLLPPAGERPPLLGERRGALERGARGGPGSVELAHLHGILRRRQLYCR
TGFHLQILPDGSVQGTRQDHSLFGILEFISVAVGLVSIRGVDSGLYLGMNGKGELYGSEKLTSECIFREQFE
ENWYNTYSSNIYKHGDTGRRYFVALNKDGTPRDGARSKRHQKFTHFLPRPVDPERVPELYKDLLVYTG

Figure 8

```
              humanFGF-20  DNA (coding)
Sequence Size  : 636

10        20        30        40        50        60
    atggctcccttagccgaagtcgggggctttctgggcggcctggagggcttgggccagcag
     M  A  P  L  A  E  V  G  G  F  L  G  G  L  E  G  L  G  Q  Q 70        80        90       100       110       120
    gtgggttcgcatttcctgttgcctcctgccggggagcggccgccgctgctgggcgagcgc
     V  G  S  H  F  L  L  P  P  A  G  E  R  P  P  L  L  G  E  R 130       140       150       160       170       180
    aggagcgcggcggagcggagcgcgcgcggcggggccggggctgcgcagctggcgcacctg
     R  S  A  A  E  R  S  A  R  G  G  P  G  A  A  Q  L  A  H  L 190       200       210       220       230       240
    cacggcatcctgcgccgccggcagctctattgccgcaccggcttccacctgcagatcctg
     H  G  I  L  R  R  R  Q  L  Y  C  R  T  G  F  H  L  Q  I  L 250       260       270       280       290       300
    cccgacggcagcgtgcagggcacccggcaggaccacagcctcttcggtatcttggaattc
     P  D  G  S  V  Q  G  T  R  Q  D  H  S  L  F  G  I  L  E  F 310       320       330       340       350       360
    atcagtgtggcagtgggactggtcagtattagaggtgtggacagtggtctctatcttgga
     I  S  V  A  V  G  L  V  S  I  R  G  V  D  S  G  L  Y  L  G 370       380       390       400       410       420
    atgaatgacaaaggagaactctatggatcagagaaacttacttccgaatgcatctttagg
     M  N  D  K  G  E  L  Y  G  S  E  K  L  T  S  E  C  I  F  R 430       440       450       460       470       480
    gagcagtttgaagagaactggtataacacctattcatctaacatatataaacatggagac
     E  Q  F  E  E  N  W  Y  N  T  Y  S  S  N  I  Y  K  H  G  D 490       500       510       520       530       540
    actggccgcaggtattttgtggcacttaacaaagacggaactccaagagatggcgccagg
     T  G  R  R  Y  F  V  A  L  N  K  D  G  T  P  R  D  G  A  R 550       560       570       580       590       600
    tccaagaggcatcagaaatttacacatttcttacctagaccagtggatccagaaagagtt
     S  K  R  H  Q  K  F  T  H  F  L  P  R  P  V  D  P  E  R  V 610       620       630       640
    ccagaattgtacaaggacctactgatgtacacttga
     P  E  L  Y  K  D  L  L  M  Y  T  *
```

Figure 9

```
rat FGF-20    MAPLTEVGAFLGGLEGLGQQVGSHFLLPPAGERPPLLGERRGALERGARGGPGSVELAHL    60
              ****  ****  ************************  *  *  ********   ****
human FGF-20  MAPLAEVGGFLGGLEGLGQQVGSHFLLPPAGERPPLLGERRSAAERSARGGPGAAQLAHL  60

HGILRRRQLYCRTGFHLQILPDGSVQGTRQDHSLFGILEFISVAVGLVSIRGVDSGLYLG  120
              ************************************************************
              HGILRRRQLYCRTGFHLQILPDGSVQGTRQDHSLFGILEFISVAVGLVSIRGVDSGLYLG  120

MNGKGELYGSEKLTSECIFREQFEENWYNTYSSNIYKHGDTGRRYFVALNKDGTPRDGAR  180
              ** ********************************************************
              MNDKGELYGSEKLTSECIFREQFEENWYNTYSSNIYKHGDTGRRYFVALNKDGTPRDGAR  180

SKRHQKFTHFLPRPVDPERVPELYKDLLVYTG  212
              ***************************  **
              SKRHQKFTHFLPRPVDPERVPELYKDLLMYT  211
```

Figure 10

Codon usage for enteric bacterial (highly expressed) genes 7/19/83

| AmAcid | Codon | Number | /1000 | Fraction |
|--------|-------|--------|-------|----------|
| Gly | GGG | 13.00 | 1.89 | 0.02 |
| Gly | GGA | 3.00 | 0.44 | 0.00 |
| Gly | GGU | 365.00 | 52.99 | 0.59 |
| Gly | GGC | 238.00 | 34.55 | 0.38 |
| Glu | GAG | 108.00 | 15.68 | 0.22 |
| Glu | GAA | 394.00 | 57.20 | 0.78 |
| Asp | GAU | 149.00 | 21.63 | 0.33 |
| Asp | GAC | 298.00 | 43.26 | 0.67 |
| Val | GUG | 93.00 | 13.50 | 0.16 |
| Val | GUA | 146.00 | 21.20 | 0.26 |
| Val | GUU | 289.00 | 41.96 | 0.51 |
| Val | GUC | 38.00 | 5.52 | 0.07 |
| Ala | GCG | 161.00 | 23.37 | 0.26 |
| Ala | GCA | 173.00 | 25.12 | 0.28 |
| Ala | GCU | 212.00 | 30.78 | 0.35 |
| Ala | GCC | 62.00 | 9.00 | 0.10 |
| Arg | AGG | 1.00 | 0.15 | 0.00 |
| Arg | AGA | 0.00 | 0.00 | 0.00 |
| Ser | AGU | 9.00 | 1.31 | 0.03 |
| Ser | AGC | 71.00 | 10.31 | 0.20 |
| Lys | AAG | 111.00 | 16.11 | 0.26 |
| Lys | AAA | 320.00 | 46.46 | 0.74 |
| Asn | AAU | 19.00 | 2.76 | 0.06 |
| Asn | AAC | 274.00 | 39.78 | 0.94 |
| Met | AUG | 170.00 | 24.68 | 1.00 |
| Ile | AUA | 1.00 | 0.15 | 0.00 |
| Ile | AUU | 70.00 | 10.16 | 0.17 |
| Ile | AUC | 345.00 | 50.09 | 0.83 |
| Thr | ACG | 25.00 | 3.63 | 0.07 |
| Thr | ACA | 14.00 | 2.03 | 0.04 |

Figure 10 (continued)

| AmAcid | Codon | Number | /1000 | Fraction |
|---|---|---|---|---|
| Thr | ACU | 130.00 | 18.87 | 0.35 |
| Thr | ACC | 206.00 | 29.91 | 0.55 |
| Trp | UGG | 55.00 | 7.98 | 1.00 |
| End | UGA | 0.00 | 0.00 | 0.00 |
| Cys | UGU | 22.00 | 3.19 | 0.49 |
| Cys | UGC | 23.00 | 3.34 | 0.51 |
| End | UAG | 0.00 | 0.00 | 0.00 |
| End | UAA | 0.00 | 0.00 | 0.00 |
| Tyr | UAU | 51.00 | 7.40 | 0.25 |
| Tyr | UAC | 157.00 | 22.79 | 0.75 |
| Leu | UUG | 18.00 | 2.61 | 0.03 |
| Leu | UUA | 12.00 | 1.74 | 0.02 |
| Phe | UUU | 51.00 | 7.40 | 0.24 |
| Phe | UUC | 166.00 | 24.10 | 0.76 |
| Ser | UCG | 14.00 | 2.03 | 0.04 |
| Ser | UCA | 7.00 | 1.02 | 0.02 |
| Ser | UCU | 120.00 | 17.42 | 0.34 |
| Ser | UCC | 131.00 | 19.02 | 0.37 |
| Arg | CGG | 1.00 | 0.15 | 0.00 |
| Arg | CGA | 2.00 | 0.29 | 0.01 |
| Arg | CGU | 290.00 | 42.10 | 0.74 |
| Arg | CGC | 96.00 | 13.94 | 0.25 |
| Gln | CAG | 233.00 | 33.83 | 0.86 |
| Gln | CAA | 37.00 | 5.37 | 0.14 |
| His | CAU | 18.00 | 2.61 | 0.17 |
| His | CAC | 85.00 | 12.34 | 0.83 |
| Leu | CUG | 480.00 | 69.69 | 0.83 |
| Leu | CUA | 2.00 | 0.29 | 0.00 |
| Leu | CUU | 25.00 | 3.63 | 0.04 |
| Leu | CUC | 38.00 | 5.52 | 0.07 |
| Pro | CCG | 190.00 | 27.58 | 0.77 |
| Pro | CCA | 36.00 | 5.23 | 0.15 |
| Pro | CCU | 19.00 | 2.76 | 0.08 |
| Pro | CCC | 1.00 | 0.15 | 0.00 |

Figure 11

Codon usage for yeast (highly expressed) genes

| AmAcid | Codon | Number | /1000 | Fraction |
|---|---|---|---|---|
| Gly | GGG | 33.00 | 0.86 | 0.01 |
| Gly | GGA | 70.00 | 1.82 | 0.02 |
| Gly | GGT | 2672.00 | 69.62 | 0.91 |
| Gly | GGC | 171.00 | 4.46 | 0.06 |
| Glu | GAG | 277.00 | 7.22 | 0.10 |
| Glu | GAA | 2442.00 | 63.63 | 0.90 |
| Asp | GAT | 1100.00 | 28.66 | 0.48 |
| Asp | GAC | 1211.00 | 31.55 | 0.52 |
| Val | GTG | 117.00 | 3.05 | 0.04 |
| Val | GTA | 75.00 | 1.95 | 0.03 |
| Val | GTT | 1548.00 | 40.33 | 0.56 |
| Val | GTC | 1026.00 | 26.73 | 0.37 |
| Ala | GCG | 36.00 | 0.94 | 0.01 |
| Ala | GCA | 203.00 | 5.29 | 0.06 |
| Ala | GCT | 2221.00 | 57.87 | 0.65 |
| Ala | GCC | 969.00 | 25.25 | 0.28 |
| Arg | AGG | 20.00 | 0.52 | 0.01 |
| Arg | AGA | 1336.00 | 34.81 | 0.83 |
| Ser | AGT | 116.00 | 3.02 | 0.05 |
| Ser | AGC | 94.00 | 2.45 | 0.04 |
| Lys | AAG | 2365.00 | 61.62 | 0.78 |
| Lys | AAA | 651.00 | 16.96 | 0.22 |
| Asn | AAT | 347.00 | 9.04 | 0.22 |
| Asn | AAC | 1259.00 | 32.80 | 0.78 |
| Met | ATG | 766.00 | 19.96 | 1.00 |
| Ile | ATA | 43.00 | 1.12 | 0.02 |
| Ile | ATT | 1223.00 | 31.87 | 0.52 |
| Ile | ATC | 1070.00 | 27.88 | 0.46 |

Figure 11 (continued)

| | | | | |
|---|---|---|---|---|
| Thr | ACG | 28.00 | 0.73 | 0.01 |
| Thr | ACA | 126.00 | 3.28 | 0.06 |
| Thr | ACT | 1129.00 | 29.42 | 0.50 |
| Thr | ACC | 962.00 | 25.07 | 0.43 |
| Trp | TGG | 325.00 | 8.47 | 1.00 |
| End | TGA | 10.00 | 0.26 | 0.09 |
| Cys | TGT | 254.00 | 6.62 | 0.89 |
| Cys | TGC | 33.00 | 0.86 | 0.11 |
| End | TAG | 11.00 | 0.29 | 0.10 |
| End | TAA | 85.00 | 2.21 | 0.80 |
| Tyr | TAT | 219.00 | 5.71 | 0.19 |
| Tyr | TAC | 913.00 | 23.79 | 0.81 |
| Leu | TTG | 2202.00 | 57.38 | 0.69 |
| Leu | TTA | 576.00 | 15.01 | 0.18 |
| Phe | TTT | 432.00 | 11.26 | 0.27 |
| Phe | TTC | 1145.00 | 29.83 | 0.73 |
| Ser | TCG | 26.00 | 0.68 | 0.01 |
| Ser | TCA | 149.00 | 3.88 | 0.06 |
| Ser | TCT | 1279.00 | 33.33 | 0.52 |
| Ser | TCC | 818.00 | 21.31 | 0.33 |
| Arg | CGG | 0.00 | 0.00 | 0.00 |
| Arg | CGA | 1.00 | 0.03 | 0.00 |
| Arg | CGT | 249.00 | 6.49 | 0.15 |
| Arg | CGC | 5.00 | 0.13 | 0.00 |
| Gln | CAG | 62.00 | 1.62 | 0.05 |
| Gln | CAA | 1225.00 | 31.92 | 0.95 |
| His | CAT | 236.00 | 6.15 | 0.35 |
| His | CAC | 433.00 | 11.28 | 0.65 |
| Leu | CTG | 52.00 | 1.35 | 0.02 |
| Leu | CTA | 236.00 | 6.15 | 0.07 |
| Leu | CTT | 90.00 | 2.35 | 0.03 |
| Leu | CTC | 14.00 | 0.36 | 0.00 |

Figure 11 (continued)

| | | | | |
|---|---|---|---|---|
| Pro | CCG | 10.00 | 0.26 | 0.01 |
| Pro | CCA | 1271.00 | 33.12 | 0.80 |
| Pro | CCT | 279.00 | 7.27 | 0.18 |
| Pro | CCC | 33.00 | 0.86 | 0.02 |

Figure 12

Codon usage for Drosophila (highly expressed) genes

| AmAcid | Codon | Number | /1000 | Fraction |
|---|---|---|---|---|
| Gly | GGG | 6.00 | 0.28 | 0.00 |
| Gly | GGA | 380.00 | 18.04 | 0.22 |
| Gly | GGT | 575.00 | 27.29 | 0.34 |
| Gly | GGC | 746.00 | 35.41 | 0.44 |
| Glu | GAG | 1217.00 | 57.77 | 0.91 |
| Glu | GAA | 115.00 | 5.46 | 0.09 |
| Asp | GAT | 503.00 | 23.88 | 0.43 |
| Asp | GAC | 654.00 | 31.04 | 0.57 |
| Val | GTG | 719.00 | 34.13 | 0.45 |
| Val | GTA | 29.00 | 1.38 | 0.02 |
| Val | GTT | 226.00 | 10.73 | 0.14 |
| Val | GTC | 608.00 | 28.86 | 0.38 |
| Ala | GCG | 94.00 | 4.46 | 0.05 |
| Ala | GCA | 80.00 | 3.80 | 0.04 |
| Ala | GCT | 446.00 | 21.17 | 0.24 |
| Ala | GCC | 1277.00 | 60.61 | 0.67 |
| Arg | AGG | 48.00 | 2.28 | 0.06 |
| Arg | AGA | 12.00 | 0.57 | 0.01 |
| Ser | AGT | 16.00 | 0.76 | 0.01 |
| Ser | AGC | 267.00 | 12.67 | 0.23 |
| Lys | AAG | 1360.00 | 64.55 | 0.93 |
| Lys | AAA | 108.00 | 5.13 | 0.07 |
| Asn | AAT | 127.00 | 6.03 | 0.13 |
| Asn | AAC | 878.00 | 41.67 | 0.87 |
| Met | ATG | 387.00 | 18.37 | 1.00 |
| Ile | ATA | 4.00 | 0.19 | 0.00 |
| Ile | ATT | 390.00 | 18.51 | 0.29 |
| Ile | ATC | 969.00 | 45.99 | 0.71 |

Figure 12 (continued)

| | | | | |
|---|---|---|---|---|
| Thr | ACG | 114.00 | 5.41 | 0.08 |
| Thr | ACA | 34.00 | 1.61 | 0.02 |
| Thr | ACT | 164.00 | 7.78 | 0.11 |
| Thr | ACC | 1127.00 | 53.49 | 0.78 |
| Trp | TGG | 243.00 | 11.53 | 1.00 |
| End | TGA | 1.00 | 0.05 | 0.01 |
| Cys | TGT | 20.00 | 0.95 | 0.08 |
| Cys | TGC | 220.00 | 10.44 | 0.92 |
| End | TAG | 12.00 | 0.57 | 0.17 |
| End | TAA | 58.00 | 2.75 | 0.82 |
| Tyr | TAT | 113.00 | 5.36 | 0.16 |
| Tyr | TAC | 574.00 | 27.25 | 0.84 |
| Leu | TTG | 210.00 | 9.97 | 0.12 |
| Leu | TTA | 9.00 | 0.43 | 0.01 |
| Phe | TTT | 62.00 | 2.94 | 0.09 |
| Phe | TTC | 635.00 | 30.14 | 0.91 |
| Ser | TCG | 195.00 | 9.26 | 0.17 |
| Ser | TCA | 29.00 | 1.38 | 0.02 |
| Ser | TCT | 103.00 | 4.89 | 0.09 |
| Ser | TCC | 558.00 | 26.49 | 0.48 |
| Arg | CGG | 7.00 | 0.33 | 0.01 |
| Arg | CGA | 25.00 | 1.19 | 0.03 |
| Arg | CGT | 281.00 | 13.34 | 0.34 |
| Arg | CGC | 465.00 | 22.07 | 0.55 |
| Gln | CAG | 703.00 | 33.37 | 0.91 |
| Gln | CAA | 66.00 | 3.13 | 0.09 |
| His | CAT | 88.00 | 4.18 | 0.22 |
| His | CAC | 312.00 | 14.81 | 0.78 |
| Leu | CTG | 1182.00 | 56.10 | 0.69 |
| Leu | CTA | 21.00 | 1.00 | 0.01 |
| Leu | CTT | 55.00 | 2.61 | 0.03 |
| Leu | CTC | 224.00 | 10.63 | 0.13 |

Figure 12 (continued)

| Pro | CCG | 84.00 | 3.99 | 0.09 |
| --- | --- | --- | --- | --- |
| Pro | CCA | 135.00 | 6.41 | 0.15 |
| Pro | CCT | 72.00 | 3.42 | 0.08 |
| Pro | CCC | 626.00 | 29.71 | 0.68 |

SEQUENCE LISTING

```
<160> NUMBER OF SEQ ID NOS: 17

<210> SEQ ID NO 1
<211> LENGTH: 648
<212> TYPE: DNA
<213> ORGANISM: Rattus norvegicus

<400> SEQUENCE: 1
ccttccatgg ctcccttgac cgaagtcggt gccttcttgg gcggcctgga gggcttgggc      60
cagcaggtgg ggtcgcactt cttgctgcct cctgcagggg agcgaccgcc gctgctaggg     120
gagcggcggg gcgcgttgga gcggggcgcc cgcggcgggc cgggttccgt ggagctggcg     180
cacctgcacg gcatcctgcg ccgccggcag ctctactgcc gcaccggctt ccacctgcag     240
atcctgcccg acggcagtgt gcagggcacc cggcaggatc acagcctctt cggtatcctg     300
gaattcatca gtgtggcggt ggggctggtc agtatcagag gtgtggacag cggcctgtac     360
cttggcatga atgcaaagg agagctttat ggctcagaga aattgacttc tgaatgcatc     420
ttcagggaac aatttgaaga gaactggtat aatacctatt catccaacat atacaaacac     480
ggagacacag gtcgcaggta ttttgtagca cttaacaaag acgggactcc aagggacggt     540
gccaggtcca aaagacacca aaagtttacc cattttttac ccagaccagt ggacccagag     600
agagtcccag agttatacaa agacctactg gtgtacactg gatgaacc                  648

<210> SEQ ID NO 2
<211> LENGTH: 212
<212> TYPE: PRT
<213> ORGANISM: Rattus norvegicus
```

-continued

```
<400> SEQUENCE: 2

Met Ala Pro Leu Thr Glu Val Gly Ala Phe Leu Gly Gly Leu Glu Gly
 1               5                  10                  15

Leu Gly Gln Gln Val Gly Ser His Phe Leu Pro Pro Ala Gly Glu
            20                  25                  30

Arg Pro Pro Leu Leu Gly Glu Arg Gly Ala Leu Glu Arg Gly Ala
        35                  40                  45

Arg Gly Gly Pro Gly Ser Val Glu Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Gly Lys Gly Glu Leu Tyr
        115                 120                 125

Gly Ser Glu Lys Leu Thr Ser Glu Cys Ile Phe Arg Glu Gln Phe Glu
130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Val Tyr Thr Gly
    210

<210> SEQ ID NO 3
<211> LENGTH: 636
<212> TYPE: DNA
<213> ORGANISM: Homo sapiens

<400> SEQUENCE: 3
atggctccct tagccgaagt cggggggcttt ctgggcggcc tggagggctt gggccagcag      60
gtgggttcgc atttcctgtt gcctcctgcc ggggagcggc cgccgctgct gggcgagcgc     120
aggagcgcgg cggagcggag cgcgcgcggc gggccggggg ctgcgcagct ggcgcacctg     180
cacggcatcc tgcgccgccg gcagctctat tgccgcaccg gcttccacct gcagatcctg     240
cccgacggca gcgtgcaggg cacccggcag gaccacagcc tcttcggtat cttggaattc     300
atcagtgtgg cagtgggact ggtcagtatt agaggtgtgg acagtggtct ctatcttgga     360
atgaatgaca aggagaact  ctatggatca gagaaactta cttccgaatg catctttagg     420
gagcagtttg aagagaactg gtataacacc tattcatcta acatatataa acatggagac     480
actggccgca ggtattttgt ggcacttaac aaagacggaa ctccaagaga tggcgccagg     540
tccaagaggc atcagaaatt tacacatttc ttacctagac cagtggatcc agaaagagtt     600
ccagaattgt acaaggacct actgatgtac acttga                                636

<210> SEQ ID NO 4
<211> LENGTH: 211
<212> TYPE: PRT
<213> ORGANISM: Homo sapiens
```

-continued

```
<400> SEQUENCE: 4

Met Ala Pro Leu Ala Glu Val Gly Gly Phe Leu Gly Leu Glu Gly
  1               5                  10                  15

Leu Gly Gln Gln Val Gly Ser His Phe Leu Pro Pro Ala Gly Glu
             20                  25                  30

Arg Pro Pro Leu Leu Gly Glu Arg Arg Ser Ala Ala Glu Arg Ser Ala
         35                  40                  45

Arg Gly Gly Pro Gly Ala Ala Gln Leu Ala His Leu His Gly Ile Leu
     50                  55                  60

Arg Arg Arg Gln Leu Tyr Cys Arg Thr Gly Phe His Leu Gln Ile Leu
 65                  70                  75                  80

Pro Asp Gly Ser Val Gln Gly Thr Arg Gln Asp His Ser Leu Phe Gly
                 85                  90                  95

Ile Leu Glu Phe Ile Ser Val Ala Val Gly Leu Val Ser Ile Arg Gly
                100                 105                 110

Val Asp Ser Gly Leu Tyr Leu Gly Met Asn Asp Lys Gly Glu Leu Tyr
            115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
        210

<210> SEQ ID NO 5
<211> LENGTH: 14
<212> TYPE: PRT
<213> ORGANISM: Artificial Sequence
<220> FEATURE:
<223> OTHER INFORMATION: Oligopeptides for raising antibodies

<400> SEQUENCE: 5

Arg Asp Gly Ala Arg Ser Lys Arg His Gln Lys Phe Thr His
  1               5                  10

<210> SEQ ID NO 6
<211> LENGTH: 15
<212> TYPE: PRT
<213> ORGANISM: Artificial Sequence
<220> FEATURE:
<223> OTHER INFORMATION: Oligopeptides for raising antibodies

<400> SEQUENCE: 6

Gln Leu Ala His Leu His Gly Ile Leu Arg Arg Arg Gln Leu Tyr
  1               5                  10                  15

<210> SEQ ID NO 7
<211> LENGTH: 10
<212> TYPE: PRT
<213> ORGANISM: Artificial Sequence
<220> FEATURE:
<223> OTHER INFORMATION: Residues which can be incorporated into FGF-20
      to allow myc monoclonal antibody-based affinity purification.
```

-continued

```
<400> SEQUENCE: 7

Glu Gln Lys Leu Ile Ser Glu Glu Asp Leu
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: Preferred thrombin cleavage site.

<400> SEQUENCE: 8

Leu Val Pro Arg Gly
 1               5

<210> SEQ ID NO 9
<211> LENGTH: 10
<212> TYPE: PRT
<213> ORGANISM: Artificial Sequence
<220> FEATURE:
<223> OTHER INFORMATION: Sequence which can be incorporated to allow for
      puficiation of FGF-20 because of its ablility to bind to
      paramagentic streptavidin beads.

<400> SEQUENCE: 9

Ser Ala Trp Arg His Pro Gln Phe Gly Gly
 1               5                  10

<210> SEQ ID NO 10
<211> LENGTH: 6
<212> TYPE: PRT
<213> ORGANISM: Artificial Sequence
<220> FEATURE:
<223> OTHER INFORMATION: Consensus amino acid sequences used to create
      sense and anti-sense PCR primers.

<400> SEQUENCE: 10

Phe Glu Glu Asn Trp Tyr
 1               5

<210> SEQ ID NO 11
<211> LENGTH: 6
<212> TYPE: PRT
<213> ORGANISM: Artificial Sequence
<220> FEATURE:
<223> OTHER INFORMATION: Consensus amino acid sequences used to create
      sense and anti-sense PCR primers.

<400> SEQUENCE: 11

Thr His Phe Leu Pro Arg
 1               5

<210> SEQ ID NO 12
<211> LENGTH: 6
<212> TYPE: PRT
<213> ORGANISM: Artificial Sequence
<220> FEATURE:
<223> OTHER INFORMATION: Consensus amino acid sequences used to create
      sense and anti-sense PCR primers.

<400> SEQUENCE: 12

Glu Asn Trp Tyr Asn Thr
 1               5

<210> SEQ ID NO 13
<211> LENGTH: 6
```

```
<212> TYPE: PRT
<213> ORGANISM: Artificial Sequence
<220> FEATURE:
<223> OTHER INFORMATION: Consensus amino acid sequences used to create
      sense and anti-sense PCR primers.

<400> SEQUENCE: 13

His Gln Lys Phe Thr His
 1               5

<210> SEQ ID NO 14
<211> LENGTH: 13
<212> TYPE: PRT
<213> ORGANISM: Artificial Sequence
<220> FEATURE:
<223> OTHER INFORMATION: E-tag

<400> SEQUENCE: 14

Gly Ala Pro Val Pro Tyr Pro Asp Pro Leu Glu Pro Arg
 1               5                  10

<210> SEQ ID NO 15
<211> LENGTH: 6
<212> TYPE: PRT
<213> ORGANISM: Artificial Sequence
<220> FEATURE:
<223> OTHER INFORMATION: His tag

<400> SEQUENCE: 15

His His His His His His
 1               5

<210> SEQ ID NO 16
<211> LENGTH: 208
<212> TYPE: PRT
<213> ORGANISM: Rattus norvegicus

<400> SEQUENCE: 16

Met Ala Pro Leu Gly Glu Val Gly Ser Tyr Phe Gly Val Gln Asp Ala
 1               5                  10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
        50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
```

```
                      180                 185                 190
Asp Pro Asp Lys Val Pro Glu Leu Tyr Lys Asp Ile Leu Ser Gln Ser
            195                 200                 205

<210> SEQ ID NO 17
<211> LENGTH: 207
<212> TYPE: PRT
<213> ORGANISM: Rattus norvegicus

<400> SEQUENCE: 17

Met Ala Glu Val Gly Gly Val Phe Ala Ser Leu Asp Trp Asp Leu Gln
  1               5                  10                  15

Gly Phe Ser Ser Leu Gly Asn Val Pro Leu Ala Asp Ser Pro Gly
                 20                  25                  30

Phe Leu Asn Glu Arg Leu Gly Gln Ile Glu Gly Lys Leu Gln Arg Gly
                 35                  40                  45

Ser Pro Thr Asp Phe Ala His Leu Lys Gly Ile Leu Arg Arg Arg Gln
         50                  55                  60

Leu Tyr Cys Arg Thr Gly Phe His Leu Glu Ile Phe Pro Asn Gly Thr
 65                  70                  75                  80

Val His Gly Thr Arg His Asp His Ser Arg Phe Gly Ile Leu Glu Phe
                     85                  90                  95

Ile Ser Leu Ala Val Gly Leu Ile Ser Ile Arg Gly Val Asp Ser Gly
                100                 105                 110

Leu Tyr Leu Gly Met Asn Glu Arg Gly Glu Leu Phe Gly Ser Lys Lys
            115                 120                 125

Leu Thr Arg Glu Cys Val Phe Arg Glu Gln Phe Glu Glu Asn Trp Tyr
        130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
            180                 185                 190

Pro Ser Lys Leu Pro Ser Met Ser Arg Asp Leu Phe Arg Tyr Arg
            195                 200                 205
```

HUMAN FGF-20 GENE AND GENE EXPRESSION PRODUCTS

CROSS-REFERENCE TO RELATED APPLICATIONS

This application claims priority from U.S. patent application Ser. No. 60/161,162 filed Oct. 22, 1999, and U.S. patent application Ser. No. 60/187,856 filed Mar. 8, 2000, which are incorporated by reference herein in their entirety.

TECHNICAL FIELD

The present invention relates to nucleic acid sequences encoding members of the fibroblast growth factor (FGF) family, and to polypeptides encoded by the nucleic acid sequences.

BACKGROUND OF THE INVENTION

The substantia nigra is an area of the brain that has generated intensive research. Interest in the substantia nigra was originally based on the finding that degeneration of dopaminergic neurons in the area causes Parkinson's disease. In addition, the substantia nigra has been strongly implicated in thought and affective disorders (1). Therefore, neurotrophic factors for dopaminergic neurons in the substantia nigra are of substantial clinical interest.

Glial cell fine-derived neurotrophic factor (GDNF) is the first neurotrophic factor documented to enhance the survival of midbrain dopaminergic neurons (Lin, L.-F. H. et al., *Science* 260:1130–1132 (1993)). Persephin, Artemin, BDGF and NT-3 also enhance the survival of midbrain dopaminergic neurons and have clinical potential in the treatment of Parkinson's disease (Milbrandt, J. et al., *Neuron* 20:245–253 (1998); Baloh,; R. H. et al., *Neuron* 21:1291–1302 (1998); Hyman, C. et al., *Nature* 350:230–232 (1991); Hyman, C. et al., *J. Neurosci.* 14:335–347 (1994)). However, GDNF was reported to be widely expressed in neurons of the brain (Pochon, N. A. et al., *Eur. J. Neurosci.* 9:463–471 (1997)). Persephin was also widely expressed in several major tissues including heart, kidney, liver and brain (Milbrandt, J. et al., *Neuron* 20:245–253 (1998)). Artemin in brain was expressed in the basal ganglia and thalamus, suggesting that it influences the subcortical motor system (Baloh, R. H. et al., *Neuron* 21:1291–1302 (1998)). BDNF and NT-3 were predominantly expressed in the hippocampus (Emfors, P. et al., *Neuron* 5:511–526 (1990)). Therefore, these neurotrophic factors appear not to be specific for dopaminergic neurons in the substantia nigra.

The prototypic fibroblast growth factors (FGFs), FGF-1 (aFGF) and FGF-2 (bFGF), were originally isolated from brain and pituitary as mitogens for fibroblasts. However, FGF-1 and FGF-2 are widely expressed in developing and adult tissues, and are polypeptides with multiple biological activities including angiogenesis, mitogenesis, cellular differentiation and repair of tissue injury (Baird, A. et al., *Cancer Cells* 3:239–243 (1991); Burgess, W. H. et al., *Annu. Rev. Biochem.* 58:575–606 (1989)). According to the published literature, the FGF family now consists of at least nineteen members, FGF-1 to FGF-19 (Dickson, C. et al., *Ann. NY Acad. Sci.* 638:18–26 (1991); Yoshida, T. et al., *Ann. NY Acad. Sci.* 638:27–37 (1991); Goldfarb, M. et al., *Ann. NY Acad. Sci.* 638:38–52 (1991); Coulier, F. et al., *Ann. NY Acad. Sci.* 638:53–61 (1991); Aaronson, S. A. et al., *Ann. NY Acad. Sci.* 638:62–77 (1991); Tanaka, A. et al., *Proc. Natl. Acad. Sci. USA* 89:8928–8932 (1992); Miyamoto, M. et al., *Mol. Cell. Biol.* 13:4251–4259 (1993); Yamasaki, M. et al., *J. Biol. Chem.* 271:15918–15921 (1996); Smallwood, P. M. et al., *Proc. Natl. Acad Sci. USA* 93:9850–9857 (1996); McWhirter, J. R. et al., *Development* 124:3221–3232 (1997); Miyake, A. et al., *Biochem. Biophys. Res. Commun.* 243:148–152 (1998); Hoshikawa, M. et al., *Biochem. Biophys. Res. Commun.* 244:187–191 (1998); Ohbayashi, N. et al., *J. Biol. Chem.* 273:18161–18164 (1998); Nishimura, T. et al., *Biochim. Biophys. Acta* 1444:148–151 (1999)). FGF-3 was identified to be a common target for activation by the mouse mammary tumor virus (Dickson, C. et al., *Ann. NY Acad. Sci.* 638:18–26 (1991)). FGF-4 to FGF-6 were identified as oncogene products (Yoshida, T. et al., *Ann. NY Acad. Sci.* 638:27–37 (1991); Goldfarb, M. et al., *Ann. NY Acad. Sci.* 638:38–52 (1991); Coulier, F. et al., *Ann. NY Acad. Sci.* 638:53–61 (1991)). FGF-10 was identified from rat lung by homology-based polymerase chain reaction (PCR) (Yamasaki, M. et al., *J. Biol. Chem.* 271:15918–15921 (1996)). FGF-11 to FGF-14 (FGF homologous factors (FHFs) 1 to 4) were identified from human retina by a combination of random cDNA sequencing, data base searches and homology-based PCR (Smallwood, P. M. et al., *Proc. Natl. Acad. Sci. USA* 93:9850–9857 (1996)). FGF-15 was identified as a downstream target of a chimeric homeodomain oncoprotein (McWhirter, J. R. et al., *Development* 124:3221–3232 (1997)). FGF-16, FGF-17, and FGF-18 were identified from rat heart and embryos by homology-based PCR, respectively (Miyake, A. et al., *Biochem. Biophys. Res. Commun.* 243:148–152 (1998); Hoshikawa, M. et al., *Biochem. Biophys. Res. Commun.* 244:187–191 (1998); Ohbayashi, N. et al., *J. Biol. Chem.* 273:18161–18164 (1998)). Recently, FGF-19 was identified from human fetal brain by data base search (Nishimura, T. et al., *Biochim. Biophys. Acta* 1444:148–151(1999)). They have a conserved ~120-amino acid residue core with ~30 to 60% amino acid identity. These FGFs also appear to play important roles in both developing and adult tissues. Thus, there is a need in the art for additional FGF molecules having functions and activities that differ from the known FGFs and for FGF molecules specifically expressed in regions of the brain implicated in human disease.

SUMMARY OF THE INVENTION

The present invention provides a composition comprising an isolated polynucleotide selected from the group consisting of:

(a) a polynucleotide comprising at least eight contiguous nucleotides of SEQ ID NO:1 or 3;

(b) a polynucleotide that encodes a variant of the polypeptide encoded by (a); and (c) a polynucleotide encoding a protein expressed by a polynucleotide having the sequence of SEQ ID NO:1 or 3.

The invention further provides for the use of the isolated polynucleotides or fragments thereof as diagnostic probes or as primers.

The present invention also provides a composition comprising a polypeptide, wherein said polypeptide is selected from the group consisting of:

(a) a polypeptide comprising at least 6 contiguous amino acids encoded by SEQ ID NO:1 or 3;

(b) a polypeptide encoded by a polynucleotide comprising SEQ ID NO:1 or 3; and (c) a variant of the polypeptide of (a) or (b).

Polypeptides of the invention are shown in SEQ ID NO:2 and 4. Other polypeptides comprise fragments of SEQ ID NO:2 and 4.

In certain preferred embodiments of the invention, the polynucleotide is operably linked to an expression control sequence. The invention further provides a host cell, including bacterial, yeast, insect and mammalian cells, transformed with the polynucleotide sequence. The invention also provides full-length cDNA and full-length polynucleotides corresponding to SEQ ID NO:1 or 3.

Protein and polypeptide compositions of the invention may further comprise a pharmaceutically acceptable carrier. Compositions comprising an antibody that specifically reacts with such protein or polypeptide are also provided by the present invention.

The invention also provides for the production of large amounts of otherwise minor cell populations of cells to be used for generation of cDNA libraries for the isolation of rare molecules expressed in the precursors cell or progeny; cells produced by treatment may directly express growth factors or other molecules, and conditioned media is screened in assays for novel activities.

The invention further provides for the isolation, self-renewal and survival of mammalian neural stem cells and the differentiation of their progeny.

The invention also provides for compositions and methods of preventing or slowing degeneration of or increasing the numbers of dopaminergic neurons, such as in the substantial nigra, in disease states including Parkinson's disease.

The invention further provides for compositions and methods of preventing or slowing degeneration of, or for enhancing the growth of, cells in the inner ear.

BRIEF DESCRIPTION OF THE DRAWINGS

FIG. 1. Amino acid sequence comparison of rat FGF-20 with rat FGF-9 and FGF-16. Numbers refer to amino acid positions of FGF-9, FGF-16 and FGF-20. Asterisks indicate identical amino acid residues of the sequences.

FIG. 6. FIG. 6 provides the DNA sequence (SEQ ID NO:1) of rat FGF-20.

FIG. 7. FIG. 7 provides the amino acid sequence (SEQ ID NO:2) of rat FGF-20.

FIG. 8. FIG. 8 provides the DNA (SEQ ID NO:3) and amino acid (SEQ ID NO:4) sequences of human FGF-20.

FIG. 9. FIG. 9 provides an alignment of the amino acid sequences of human (SEQ ID NO:4) and rat (SEQ ID NO:2) FGF-20.

FIG. 10. FIG. 10 provides codon usage for E. coli.

FIG. 11. FIG. 11 provides codon usage for yeast. The first field of information on each line of the table contains a three-letter code for an amino acid. The second field contains an unambiguous codon for that amino acid. The third field lists the number of occurrences of that codon in the genes from which the table is compiled. The fourth field lists the expected number of occurrences of that codon per 1,000 codons in genes whose codon usage is identical to that compiled in the codon frequency table. The last field contains the fraction of occurrences of the codon in its synonymous codon family.

FIG. 12. FIG. 12 provides codon usage for Drosophila.

DETAILED DESCRIPTION OF THE INVENTION

Figure 2:
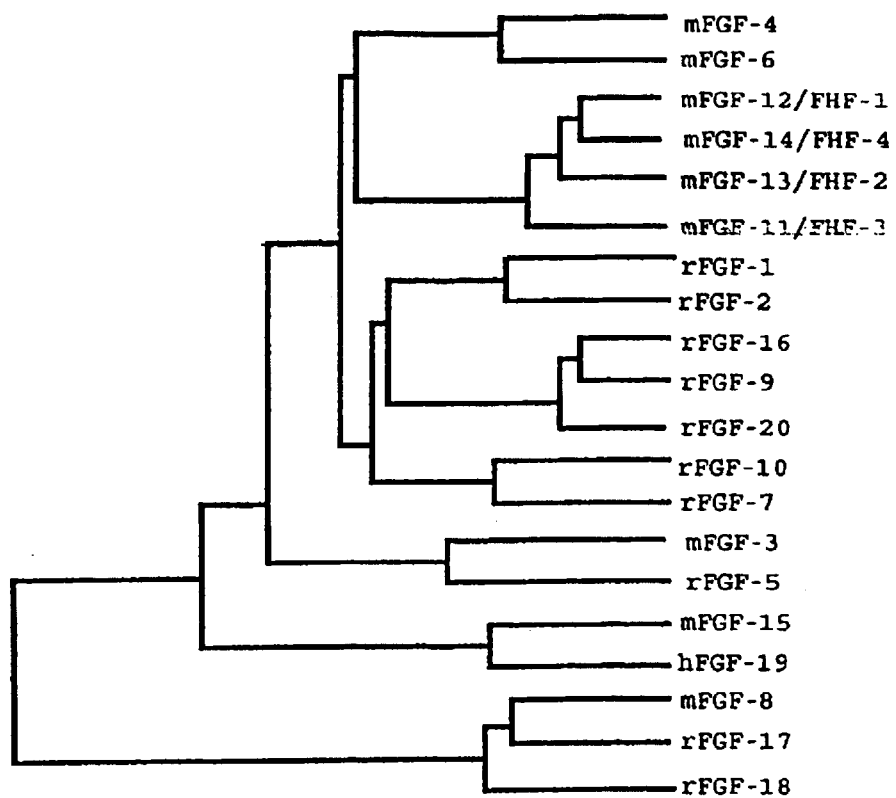
FIG. 2. The apparent evolutionary relationships of 20 members of the FGF family. The length of each horizontal line is proportional to the degree of amino acid sequence divergence. mFGF, rFGF, and hFGF indicate mouse FGF, rat FGF, and human FGF, respectively.

Because of their potent activities for promoting growth, proliferation, survival and differentiation of a wide variety of cells and tissue types, FGFs continue to be pursued as therapeutic agents for a number of different indications, including wound healing, such as musculo-skeletal conditions, for example, bone-fractures, ligament and tissue repair, tendonitis, bursitis, etc.; skin conditions, for example, burns, cuts, lacerations, bed sores, slow healing ulcers, etc.; tissue protection and repair during myocardial infarction and ischemia, in the treatment of neurological conditions, for example, neuro-degenerative disease and stroke, in the treatment of eye disease, including macular degeneration, and the like.

The fibroblast growth factor (FGF) proteins identified to date belong to a family of signaling molecules that regulate growth and differentiation of a variety of cell types. The significance of FGF proteins to human physiology and pathology relates in part to their key roles in embryogenesis, in blood vessel development and growth, and in bone growth. In vitro experiments have demonstrated a role for FGF in regulating cell growth and division of endothelial cells, vascular smooth muscle cells, fibroblasts, and cardiac and skeletal myocytes. Other members of the FGF family and their biological roles are described in Crossley et al., *Development* 121:439–451 (1995); Ohuchi et al., *Development* 124:2235–2244 (1997); Gemel et al., *Genomics* 35:253–257 (1996); and Ghosh et al., *Cell Growth and Differentiation* 7:1425–1434 (1996).

FGF proteins are also significant to human health and disease because of a role in cancer cell growth. For example, FGF-8 was identified as an androgen-induced growth factor in breast and prostate cancer cells. (Tanaka et al., *FEBS Lett.* 363:226–230 (1995) and *P.N.A.S.* 89:8928–8932 (1992)).

The role of FGF in normal development is being elucidated in part through studies of FGF receptors. Wilke, T. et al., *Dev. Dynam.* 210:41–52 (1997) found that FGFR1, FGFR2, and FGFR3 transcripts were localized to specific regions of the head during embryonic development in chickens. The expression pattern correlated with areas affected by human FGFR mutations in Crouzon syndrome, a condition of abnormal intramembranous bone formation. Belluardo, N. et al., *Jour. Comp. Neur.* 379:226–246 (1997) studied localization of FGFR 1, 2, and 3 mRNAs in rat brain, and found cellular specificity in several brain regions. Furthermore, FGFR1 and FGFR2 mRNAs were expressed in astroglial reactive cells after brain lesion, supporting a role of certain FGF's in brain disease and injury. Ozawa, K. et al., *Mol. Brain Res.* 41:279–288 (1996) reported that FGF1 and FGF-5 expression increased after birth, whereas FGF3, FGF-6, FGF-7, and FGF-8 genes showed higher expression in late embryonic stages than in postnatal stages.

New members of the FGF family are described here, wherein the FGF protein is expressed in dopaminergic neurons of the substantial nigra and in cochlear tissue of rat embryos. A polynucleotide encoding the rat FGF of the invention has the sequence as shown in SEQ ID NO:1. A polynucleotide encoding the human FGF of the invention has the sequence as shown in SEQ ID NO:3. The rat polynucleotide was identified as encoding a member of the FGF family by the conserved regions throughout the amino acid sequence and by the regions of homology shared by the polynucleotides and genes encoding known FGF proteins.

The inventors believe that FGF-20 is a previously unidentified member of the FGF family. To date, over 19 human FGF proteins have been identified. In most cases, homologous proteins in the other mammals, particularly mice and rats, have also been identified. The human proteins vary to different degrees in terms of amino acid sequence, receptor specificity, tissue expression patterns, and biological activity.

The present FGF-20 differs in sequence from all the FGF proteins described to date in publications. FGF-20 shares some homology with FGF-9 and FGF-16.

As discussed herein, the knowledge about the roles played by various FGF proteins continues to grow, but is by far incomplete.

The present invention adds to this knowledge by disclosing that the FGF of SEQ ID NO:1 is highly expressed in dopaminergic neurons of the substantia nigra of brain, and human FGF-20 may play a role in development of and recovery from a neural disease, such as Parkinson's disease. FGF-20 is also preferentially expressed in rat embryo (E14.5) cochlea of the inner ear.

The invention therefore is based upon the identification, isolation, sequencing and expression patterns of a new fibroblast growth factor (FGF-20).

Isolation and Analysis of Rat cDNA encoding FGF-20 Members of the FGF family have a conserved ~120-amino acid residue core with ~30 to 70% amino acid identity. Among the members of the FGF family, FGF-9 and FGF-16 are highly homologous (73% amino acid identity). According to the invention, DNA encoding a novel rat FGF has been identified. The nucleotide sequence of the entire coding region was determined by adaptor-ligation mediated polymerase chain reaction using rat-brain cDNA as a template and cassette-ligation mediated polymerase chain reaction using rat genomic DNA as a template. The nucleotide sequence of the coding region allowed for the elucidation of the complete amino acid sequence of the FGF (212 amino acids), which has a conserved amino acid residue core (amino acids 62 to 197) (FIG. 1). Two cysteine residues that are well conserved in the FGF family are also conserved in the protein (amino acids 71 and 137) (FIG. 1). This protein is tentatively named FGF-20. FGF-20 is most similar to FGF-9 and FGF-16 (70 and 62% amino acid identity) among 19 members of the FGF family, respectively (FIG. 1). The apparent evolutionary relationships of twenty members of the FGF family are shown in FIG. 2. FGF-20 was closest to FGF-9 and FGF-16.

Figure 4:
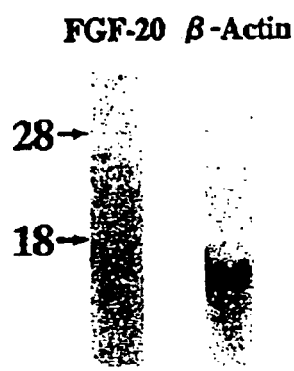
FIG. 4. Expression of FGF-20 mRNA in rat brain. Rat brain poly (A)$^+$RNA (10 μg) was electrophoresed on a denaturing agarose gel (1%) containing formaldehyde and transferred onto a nitrocellulose membrane. Hybridization was performed with a $^{32}$P labeled rat FGF-20 or β-actin cDNA probe. 28S and 18S indicate the positions of 28 and 18S rRNAs, respectively.

Expression of FGF-20 mRNA in Rat Tissues FGF-9 and FGF-16 mRNAs are preferentially expressed in rat kidney and heart, respectively (Miyamoto, M. et al., *Mol. Cell. Biol.* 13:4251–4259 (1993); Miyake, A. et al., *Biochem. Biophys. Res. Commun.* 243:148–152 (1998)). The expression of FGF-20 mRNA was examined in adult rat major tissues including brain, heart, lung, liver, kidney, and small intestine by polymerase chain reaction. FGF-20 mRNA was detected in the brain, but was undetectable or present in very low levels in other tissues. To confirm the expression of FGF-20 mRNA in rat brain, rat brain poly $(A)^+$ RNA was examined by Northern blotting analysis using a $^{32}$P-labeled rat FGF-20 cDNA probe. A faint but definite signal of FGF-20 mRNA was detected (FIG. 4). To confirm the integrity of the poly $(A)^+$ RNA, the hybridized probe was washed from the membrane, and the membrane was rehybridized with a $^{32}$P-labeled rat β-actin cDNA probe. A strong and discrete signal of β-actin mRNA was detected indicating that the poly $(A)^+$ RNA was not degraded (FIG. 4). FGF-20 mRNA was also detected in rat embryos (E14.5), specifically in the cochlea of the inner ear, using $^{35}$S-labeled FGF-20 antisense and sense cRNA probes (FIG. 10).

Figure 3:
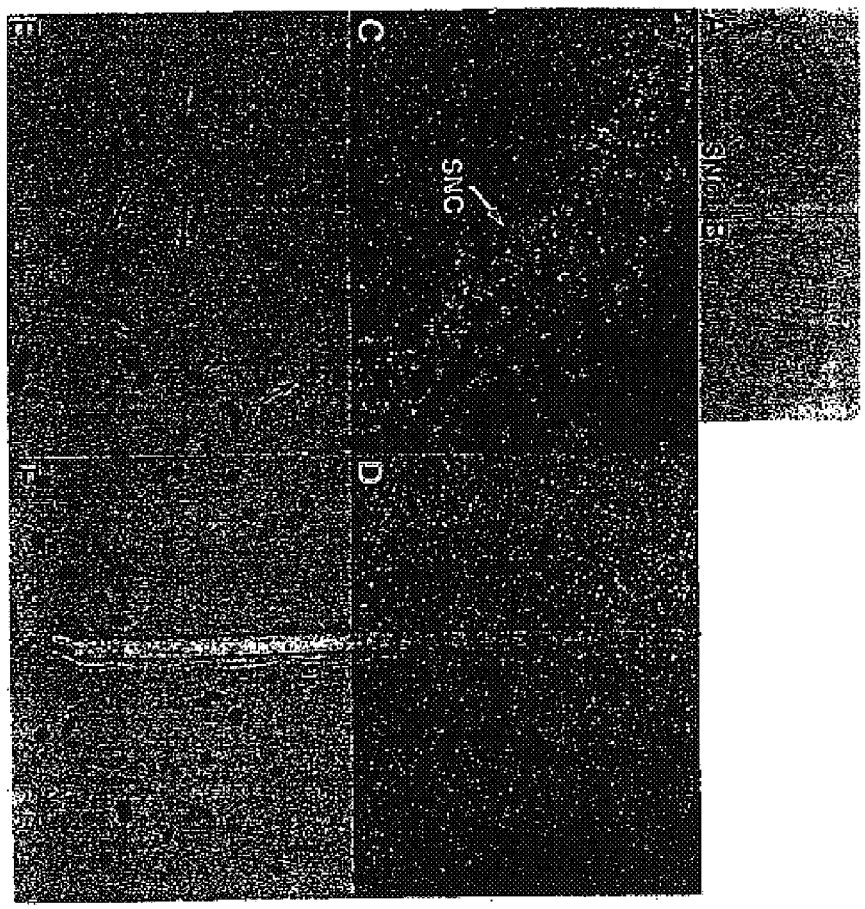
FIG. 3. Localization of FGF-20 mRNA in rat brain. (A, B) Coronal sections were hybridized with $^{35}$S-labeled FGF-20 antisense (A) and sense (B) probes, and exposed to X-ray film for 10 days. Section A is adjacent to section B. Scale bar=0.5 cm. (C, D) Sections A and B were dipped in liquid emulsion and counterstained with Cresyl violet after 3 weeks. Dark-field photographs of the SNC in sections A and B are shown in C and D, respectively. White grains in the dark-field photograph show the localization of FGF-20 mRNA. Scale bar=50 μm. SNC, substantial nigra pars compacta.

Expression of FGF-20 mRNA in Rat Brain To examine the expression of FGF-20 mRNA in rat brain, consecutive coronal sections of rat brain were analyzed by in situ hybridization with an $^{35}$S-labeled antisense or sense FGF-20 cRNA probe. Discrete specific labeling was observed only in the substantia nigra pars compacta (FIG. 3A, C). No specific labeling was observed in other brain regions examined. The cellular localization of FGF-20 mRNA was examined by microscopy at higher magnification. By Nissle staining of brain sections, glial cells can be identified as small intensely stained (dark) cells, while neurons are generally larger and less intensely stained (lighter) owing to their larger volume (Gerfen, C. R., *Methods in Neurosciences*, Academic Press, San Diego, Calif., Vol. 1, pp. 79–97 (1989)). Black grains of labeled probes were found in most neurons of these brain areas (FIG. 3E). Dopaminergic neurons in the substantial nigra are preferentially localized in the substantial nigra pars compacta (Fallon, J. H. et al., *The Rat Nervous System*, $2^{nd}$ Ed., Academic Press, San Diego, Calif., pp. 215–238 (1995)). Furthermore, neurons in the substantia nigra pars compacta predominantly consist of dopaminergic neurons (Fallon, J. H. et al., *The Rat Nervous System*, $2^{nd}$ Ed., Academic Press, San Diego, Calif., pp. 215–238 (1995)). It is expected that FGF-20 is preferentially expressed in dopaminergic neurons in the substantia nigra pars compacta.

Preparation of Recombinant Rat FGF-20. To produce recombinant rat FGF-20, High Five insect cells were infected with recombinant baculovirus containing the rat FGF-20 cDNA with the 3'-terminal extension encoding E and $His_6$ tags. To detect recombinant FGF-20 in the culture medium, the medium was examined by Western blotting analysis with anti-E tag antibodies. A major band of 26.5 kDa was detected in the culture medium. The observed molecular mass of the major band was consistent with the calculated molecular mass of recombinant FGF-20 (26,247). This result indicates that FGF-20 is secreted, although on hydropathy plot analysis (Nielsen, H. et al., *Protein Engi-* neering 10:1–6 (1997)) the value of the amino-terminal region of FGF-20 was low, suggesting that FGF-20 has no signal sequence. Although FGF-9 and FGF-16 have no typical signal sequence in their amino termini, they are also secreted (Miyamoto, M. et al., *Mol. Cell. Biol.* 13:4251–4259 (1993), Miyake, A. et al., *Biochem. Biophys. Res. Commun.* 243:148–152 (1998)). Recombinant FGF-20 was purified from the culture medium by affinity chromatograph with Ni-NTA agarose and was analyzed by SDS-polyacrylamide gel electrophoresis under reducing conditions. A 26.5 kDa protein of FGF-20 was detected.

Figure 5:
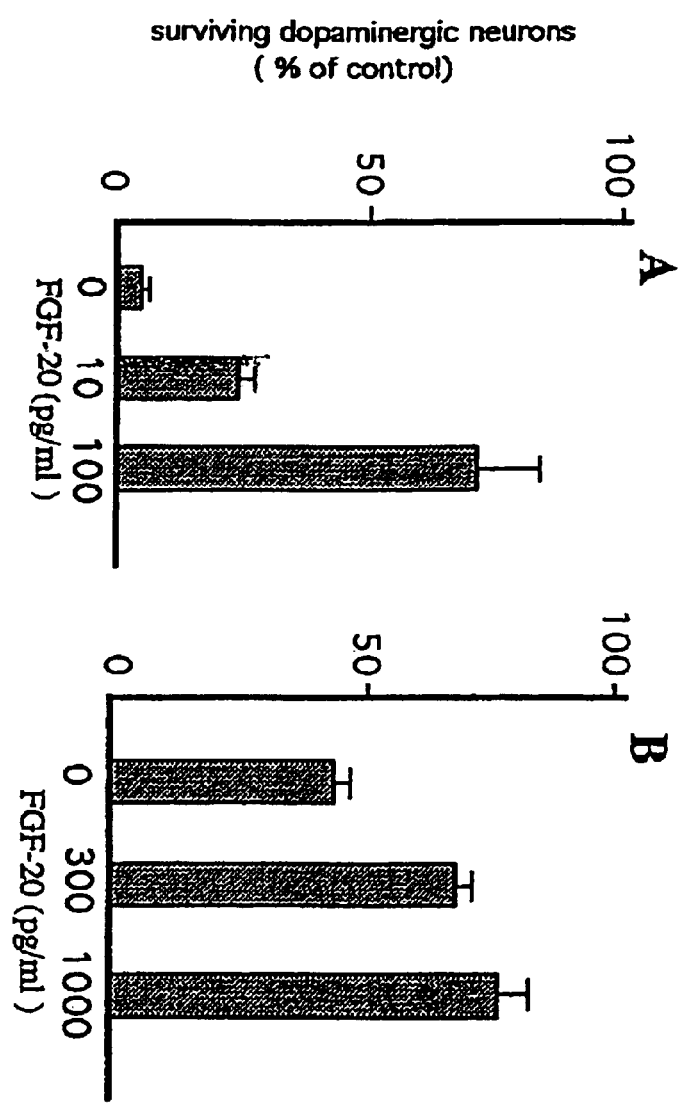
FIG. 5. FGF-20 enhances survival of midbrain dopaminergic neurons. (A) Effect of FGF-20 on survival of midbrain dopaminergic neurons in serum-free medium. Midbrain cultured cells were incubated for 4 days in medium supplemented with 10% horse serum (control) or serum-free medium supplemented with FGF-20, and then the numbers of surviving dopaminergic neurons were determined. (B) Effect of FGF-20 for 24 h, and then treated with no (control) or 1 mM glutamate for 10 min. The cultured cells were further incubated in the medium in the absence of glutamate and FGF-20 for 3 days, and then the numbers of surviving dopaminergic neurons were determined.

Neurotrophic Activity of FGF-20 for Rat Midbrain Dopaminergic Neurons FGFs are local signal molecules that act on proximal cells (Burgess, W. H. et al., *Annu. Rev. Biochem.* 58:575–606 (1989)). Therefore, it was expected that FGF-20 acts on dopaminergic neurons in the substantia nigra in autocrine and/or paracrine manner. The neurotrophic activity of FGF-20 for cultured rat midbrain dopaminergic neurons was examined. When the dopaminergic neurons were cultured in a serum-free medium for 4 days, numbers of surviving dopaminergic neurons were greatly reduced. FGF-20 significantly enhanced survival of the dopaminergic neurons in the serum-free medium (FIG. 5A). The effect of FGF-20 on glutamate-induced neuronal death in cultured rat midbrain dopaminergic neurons was also examined. When the cultured cells were exposed to 1 mM glutamate for 10 min, the numbers of surviving dopaminergic neurons were reduced. FGF-20 also significantly enhanced survival of the dopaminergic neurons exposed to toxic concentrations of glutamate (FIG. 5B).

Several FGFs are expressed in brain and expected to play important roles as neutrophic factors. FGF-1 and FGF-2 are abundant in brain (Gospodarowicz, D., *Methods Enzymol.* 147:106–119 (1987)) and exert survival enhancing effects on primary cultures from various regions of the brain (Walicke, P. A., *J. Neurosci.* 8:2618–2627 (1988)). FGF-1 is expressed predominantly in motor and sensory neurons of the midbrain and brainstem (Elde, R. et al., *Neuron* 7:349–364 (1991)). In contrast, FGF-2 is preferentially expressed in neurons in restricted regions including the cingulate cortex, industium grieum, fasciola cinererum and hippocampus, and in astrocytes in widespread regions of the brain (Emoto, N. et al., *Growth Factors* 2:21–29 (1989); Woodward, W. R. et al., *J. Neurosci.* 12:142–152 (1992)). FGF-5 is weakly expressed in the cerebral cortex, hippocampus and thalamus (Haub, O. et al., *Proc. Natl. Acad Sci. USA* 87:8022–8026 (1990)). FGF-9 and FGF-11 to FGF-14 are expressed in neurons of restricted regions including the hippocampus, thalamus, midbrain and brainstem (Yamamoto, S. et al., *Biochim. Biophys. Acta* 1398:38–41 (1998)). In contrast, FGF-20 of the invention was preferentially expressed in dopaminergic neurons of the substantia nigra. The expression profile of FGF-20 was quite distinct from those of other FGFs, indicating that FGF-20 plays a unique role in the brain.

Degeneration of dopaminergic neurons in the substantia nigra causes Parkinson's disease (Fallon, J. H. et al., *The Rat Nervous System*, $2^{nd}$ Ed., Academic Press, San Diego, Calif. pp. 215–238 (1995)). Therefore, neurotrophic factors for dopaminergic neurons in the substantia nigra have received substantial attention. GDNF, Persephin, Artemin, BDNF, and NT-3 enhance survival of midbrain dopaminergic neurons (Lin, L.-F. H. et al., *Science* 260:1130–1132 (1993); Milbrandt, J. et al., *Neuron* 20:245–253 (1998); Baloh, R. H. et al., *Neuron* 21:1291–1302 (1998); Hyman, C. et al., *Nature* 350:230–232 (1991); Hyman, C. et al., *J. Neurosci.* 14:335–347 (1994)). However, their expression is not restricted to the substantia nigra (Pochon, N. A. et al., *Eur. J. Neurosci.* 9:463–471 (1997); Milbrandt, J. et al., *Neuron* 20:245–253 (1998); Baloh, R. H. et al., *Neuron* 21:1291–1302 (1998); Emfors, P. et al., *Neuron* 5:511–526 (1990)). In contrast, the expression of FGF-20, which also enhanced the survival of midbrain dopaminergic neurons, was highly lo restricted in dopaminergic neurons in the substantia nigra pars compacta. Therefore, FGF-20 is expected to play an important role as a neurotrophic factor for dopaminergic neurons in the substantia nigra. It is therefore an important finding of the invention that FGF-20 is the first neurotrophic factor documented to be expressed preferentially in dopaminergic neurons of the substantia nigra.

It is believed that dopamine neurons are dysfunctional for, perhaps, years, before they are irreversibly damaged. (Dunnett, S. B. et al., *Nature* 399:A32-A39 (1999)) Thus, neurotrophic agents such as FGF-20 may be useful in preventing cell death or restoring function The FGF-20 may be administered using gene transfer methods to block degeneration. Such methods have been used with neurotrophic factor GDNF (glial cell line-derived neutrophic factor). In a rat Parkinson's model, nanogram amounts of BDNF and GDNF were measured from transduced cells, and the neuroprotective effect was in the order of 40–70% rescue of nigral dopamine neurons. Thus, transplants using fibroblasts or fibroblast cell lines engineered to secrete FGF-20 of the invention can allow secretion of the factor and rescue of nigral dopamine neurons. Alternatively, injection of the striatum or the substantia nigra region with viral vectors carrying the FGF-20 gene may also have a neuroprotective effect.

In Parkinson's Disease, neuronal degeneration in the substantial nigra generally is slow and protracted. This suggests that early intervention could block or slow down the degenerative process, perhaps up to 4 or 5 years before clinical symptoms appear. A decline in striatal dopamine function can be detected by PET and SPECT imaging before the appearance of clinical symptoms, providing an opportunity for neuroprotective intervention at this early stage.

In vivo imaging of dopaminergic activity in the basal ganglia, using [$^{18}$F]fluorodopa PET, can be used to monitor progress of the disease as well as the impact of treatment. A progressive reduction in fluorodopa signal is seen in brain tissue of pre-symptomatic and symptomatic individuals. After treatment with nigral tissue implant, the fluorodopa signal increases over time. (Dunnett et al., supra.) This and other techniques known in the art can be used to measure the effect of treatments described herein using to FGF-20, and the clinician will be skilled in the art of determining appropriate treatment levels and regimens.

FGF-20 Expression in Rat Embryo Cochlea FGF-20 is preferentially expressed in the cochlea of the inner ear in rat embryos (E14.5). This supports a role for FGF-20 in the development and maintenance of normal ear function. Other previously-identified members of the FGF family contribute to normal ear growth and development. For example, sensory cells in the cochlea of the rat transiently express FGF-1 during the time of terminal innervation in the sensory epithelium (Dazert et al., *J. Cell Physiol.* 177:123–129 (1998)). These authors also found that in vitro, spiral ganglion explants cultured in the presence of FGF-1 exhibited a dose-dependent increase in the number and length of neurites. In chick cochlea, FGF-1 mRNA levels increased in sensory epithelium of the cochlea in response to ototoxic damage, suggesting that the FGF system may be involved in the response of the cochlear epithelium to ototoxic damage.

Pickles et al., *Dev. Neuroscience* 19:476487 (1997). FGF-2 may help to regulate the proliferation step during hair cell development and regeneration after trauma in rats. Zheng et al., *J. Neuroscience* 25 17:216226 (1997). Thus, FGF molecules play several roles in maintaining normal development and function of the cochlea, and recovery of the cochlea from ototoxic damage. The absence of FGF receptor 3 contributes to inner ear defects in mice homozygous for skeletal and inner ear defects, including failure of pillar cell differentiation and tunnel of Corti formation, and profound deafness. Colvin et al., *Nat. Genet.* 12:390–397 (1996). It is of interest that FGF-20 of the invention binds to FGF receptor 3c (Example 12). The fact that FGF-20 is expressed at a specific stage in rat inner ear development further suggests its importance in development of this tissue.

FGF-20 therefore may be suitable for treating a variety of conditions related to the ear. Currently, about 7.8 million Americans have mild hearing loss, 10 million have moderate hearing loss, and 2.7 million have profound or severe hearing loss. The causes include, but are not limited to, otosclerosis; Cogan's syndrome; Meniere's disease; Pendred's syndrome; diabetes-associated hearing loss (non-insulin-dependent diabetes mellitus in combination with obesity can cause tissue changes in the cochlea, McQueen et al., *J. Laryngol. Otol.* 113:113–118 (1999)); congenital malformations; autoimmune disease-related hearing loss; age-related hearing loss; deafness associated with lack of FGF receptor (Colvin et al., *Nat. Genet.* 12:390–397 (1996)); ischemia-related hearing disturbance; and other conditions in which cochlear structure and function plays a role. Administration of FGF-20 protein or polynucleotide may be used to treat inherited, congenital and acquired diseases of hearing and balance, by promoting the survival, proliferation or differentiation of cells of the inner ear.

Reference to FGF-20 herein is intended to be construed to include growth factors of any origin which are substantially homologous to and which are biologically equivalent to the FGF-20 characterized and described herein. Such substantially homologous growth factors may be native to any tissue or species and, similarly, biological activity can be characterized in any of a number of biological assay systems.

The term "biologically equivalent" is intended to mean that the compositions of the present invention are capable of demonstrating some or all of the same growth properties in a similar fashion, not necessarily to the same degree as the FGF-20 isolated as described herein or recombinantly produced human FGF-20 of the invention.

By "substantially homologous" it is meant that the degree of homology of human FGF-20 to FGF-20 from any species is greater than that between FGF-20 and any previously reported member of the FGF family.

Sequence identity or percent identity is intended to mean the percentage of same residues between two sequences, referenced to human FGF when determining percent identity with non-human FGF-20, referenced to FGF-20 when determining percent identity with non-FGF-20 growth factors, when the two sequences are aligned using the Clustal method (Higgins et al., *Cabios* 8:189–191 (1992)) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment= 10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of protein Sequence and Structure*, Dayhoff, Ed., NDRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to human FGF-20 when determining percent conservation with non-human FGF-20, and referenced to FGF-20 when determining percent conservation with non-FGF-20 growth factors. Conservative amino acid changes satisfying this requirement are: R-K; E-D, Y-F, L-M; V-I, Q-H.

The invention provides FGF-20 proteins or variants thereof having one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, pegylation of FGF-20 proteins and/or muteins is expected to provide such s improved properties as increased half-life, solubility, and protease resistance. FGF-20 proteins and/or muteins may alternatively be modified by the covalent addition of polymers to free amino groups such as the lysine epsilon or the N-terminal amino group. Preferred cysteines and lysines for covalent modification will be those not involved in receptor or heparin binding. In both human and rat FGF-20, the heparin binding site comprises amino acids 170–186. It will be apparent to one skilled in the art that the methods for assaying FGF-20 biochemical and/or biological activity may be employed in order to determine if modification of a particular amino acid residue affects the activity of the protein as desired.

It may be advantageous to improve the stability of FGF-20 by modifying one or more protease cleavage sites. Thus, the present invention provides FGF-26 variants in which one or more protease cleavage site has been altered by, for example, substitution of one or more amino acids at the cleavage site in order to create as FGF-20 variant with improved stability. Such improved protein stability may be beneficial during protein production and/or therapeutic use.

Suitable protease cleavage sites for modification are well known in the art and likely will vary depending on the particular application contemplated. For example, typical substitutions would include replacement of lysines or arginines with other amino acids such as alanine. The loss of activity, such as receptor binding or heparin binding, can be tested for as described herein.

FGF-20 can also include hybrid and modified forms of FGF-20 including fusion proteins and FGF-20 fragments and hybrid and modified forms in which certain amino acids have been deleted or replaced and modifications such as where one or more amino acids have been changed to a modified amino acid or unusual amino acid and modifications such as glycosylations so long as the hybrid or modified form retains the biological activity of FGF-20. By retaining the biological activity, it is meant that neuronal survival is promoted, although not necessarily at the same level of potency as that of the FGF-20 isolated as described herein or that of the recombinantly produced human FGF-20. Fusion proteins can consist of the FGF-20 of the invention or fragment thereof and a signal sequence of a heterologous protein to promote secretion of the protein product. Fusion proteins comprising FGF-20 or a biologically active or antigenic fragment thereof can be produced using methods known in the art. Such fusion proteins can be used therapeutically or can be produced in order to simplify the isolation and purification procedures. Histidine residues can be incorporated to allow immobilized metal affinity chromatography purification. Residues EQKLISEEDL. (SEQ ID NO:7) contain the antigenic. determinant recognized by the myc monoclonal antibody and can be incorporated to allow myc monoclonal antibody-based affinity purification. A thrombin cleavage site can be incorporated to allow cleavage of the molecule at a chosen site; a preferred thrombin cleavage site consists of residues LVPRG. Purification of the molecule can be facilitated by incorporating a sequence, such as residues SAWRHPQFGG (SEQ ID NO:9), which binds to paramagnetic streptavidin beads. Such embodiments are described in WO 97/25345, which is incorporated by reference.

The invention further includes chimeric molecules between FGF-20 and keratinocyte growth factor (KGF) (Reich-Slotky, R. et al., *J. Biol. Chem.* 270:29813–29818 (1995)). The chimeric molecule can contain specific regions or fragments of one or both of the FGF-20 and KGF molecules, such as the FGF-20 fragments described below.

The invention also includes fragments of FGF-20. Preferred fragments of SEQ ID NO:4 and 2 include: amino acids from about 170 to about 186; amino acids from about 1 to about 169; amino acids 2–211 (212 for SEQ ID NO:2); amino acids from about 1 to about 169 and about 187 to about 211 (212 for SEQ ID NO:2), wherein amino acids about 169 and about 187 are joined by a peptide bond; and amino acids from about 59 to about 193. Such fragments can be prepared from the protein by standard biochemical methods or by expressing a polynucleotide encoding the fragment.

FGF-20, or a fragment thereof, can be produced as a fusion protein comprising human serum albumin (HSA) or a portion thereof. Such fusion constructs are suitable for enhancing expression of the FGF-20, or fragment thereof, in an eukaryotic host cell. Exemplary HSA portions include the N-terminal polypeptide (amino acids 1–369, 1–419, and intermediate lengths starting with amino acid 1), as disclosed in U.S. Pat. No. 5,766,883, and publication WO 97/24445, incorporated by reference herein. Other chimeric polypeptides can include a HSA protein with FGF-20, or fragments thereof, attached to each of the C-terminal and N-terminal ends of the HSA. Such HSA constructs are disclosed in U.S. Pat. No. 5,876,969, incorporated by reference herein.

Also included with the scope of the invention are FGF-20 molecules that differ from native FGF-20 by virtue of changes in biologically active sites. FGF-20 has a putative heparin binding site at amino acid residues 170–186. An FGF-20 molecule that does not bind heparin can be prepared by expressing DNA encoding FGF-20, wherein the corresponding codons for amino acid residues 170–186 have been deleted. Conversely, one or more additional heparin binding sites can be added to FGF-20 by,; for example, expressing DNA encoding FGF-20 wherein the codons corresponding to residues 170–186 are inserted at the desired position(s) in the reading frame. DNA encoding FGF-20 with altered receptor binding can likewise be produced. For example, it may be desirable to alter receptor specificity of FGF-20 by substituting the receptor binding regions of a different FGF for that of FGF-20.

Also included within the meaning of substantially homologous is any FGF-20 which may be isolated by virtue of cross-reactivity with antibodies to the FGF-20 described herein or whose encoding nucleotide sequences including genomic DNA, mRNA or cDNA may be isolated through hybridization with the complementary sequence of genomic or subgenomic nucleotide sequences or cDNA of the FGF-20 herein or fragments thereof. It will also be appreciated by one skilled in the art that degenerate DNA sequences can encode human FGF-20 and these are also intended to be included within the present invention, as are mammalian allelic variants of FGF-20.

Growth factors are thought to act at specific receptors. According to the invention, FGF-20 and as yet unknown members of this family of growth factors act through specific receptors having distinct distributions as has been shown for other growth factor families. FGF-20 binds to FGF receptor 2 and FGF receptor 3, but does not bind to FGF receptor 1. Thus, its receptor binding profile differs from FGF-2 and FGF-4, which bind to FGF receptor 1.

A preferred hFGF-20 of the present invention has been identified and isolated in purified form as described. Also preferred is hFGF-20 prepared by recombinant DNA technology. By "pure form" or "purified form" or "substantially purified form" it is meant that an FGF-20 composition is substantially free of other proteins which are not FGF-20.

Recombinant human FGF-20 may be made by expressing the DNA sequences encoding FGF-20 in a suitable transformed host cell. Using methods well known in the art, the DNA encoding FGF-20 may be linked to an expression vector, transformed into a host cell and conditions established that are suitable for expression of FGF-20 by the transformed cell.

The DNA encoding FGF-20 can be engineered to take advantage of preferred codon usage of host cells. Codon usage in *Pseudomonas aeruginosa* is described in, for example, West et al., *Nucleic Acids Res.* 11:9323–9335 (1988). Codon usage in *Saccharomyces cerevisiae* is described in, for example, Lloyd et al., *Nucleic Acids Res.* 20:5289–5295 (1992). Codon preference in Corynebacteria and a comparison with *E. coli* preference is provided in Malubres et al., *Gene* 134:15–24 (1993). Codon usage in *Drosophila melanogaster* is described in, for example, Akashi, *Genetics* 136:927–935 (1994). Codon usage in yeast is also shown in FIG. 11, and codon usage in Drosophila is show in FIG. 12.

Any suitable expression vector may be employed to produce recombinant human FGF-20 such as expression vectors for use in insect cells. Baculovirus expression systems can also be employed. A preferable method is expression in insect cells, such as Tr5 or Sf9 cells, using baculovirus vector.

The present invention includes nucleic acid sequences including sequences that encode human FGF-20. Also included within the scope of this invention are sequences that are substantially the same as the nucleic acid sequences encoding FGF-20. Such substantially the same sequences may, for example, be substituted with codons more readily expressed in a given host cell such as *E. coli* according to well known and standard procedures. Such modified nucleic acid sequences are included within the scope of this invention.

Specific nucleic acid sequences can be modified by those skilled in the art and, thus, all nucleic acid sequences that code for the amino acid sequences of FGF-20 can likewise be so modified. The present invention thus also includes nucleic acid sequence which will hybridize with all such nucleic acid sequences or complements of the nucleic acid sequences where appropriate and encode a polypeptide having the neuronal cell survival promoting activities disclosed herein. The present invention also includes nucleic acid sequences that encode polypeptides that have neuronal cell survival promoting activity and that are recognized by antibodies that bind to FGF-20. Preferred methods and epitopes for raising antibodies are described in Example 10.

The present invention also encompasses vectors comprising expression regulatory elements operably linked to any of the nucleic acid sequences included within the scope of the invention. This invention also includes host cells of any variety that have been transformed with vectors comprising expression regulatory elements operably linked to any of the nucleic acid sequences included within the scope of the present invention.

Methods are also provided herein for producing FGF-20. Preparation can be by isolation from conditioned medium from a variety of cell types so long as the cell type produces FGF-20. A second and preferred method involves utilization of recombinant methods by isolating or obtaining a nucleic acid sequence encoding FGF-20, cloning the sequence along with appropriate regulatory sequences into suitable vectors and cell types, and expressing the sequence to produce FGF-20.

Although FGF-20 has been described on the basis of its ability to enhance the survival of midbrain dopaminergic neurons, this factor may act on other cell types as well. Thus, it is likely that FGF-20 can act on other neural cells.

It is also likely that FGF-20 will act on non-neuronal cells to promote their survival, growth or function. This expectation is based upon the activity of known growth factors. Members of the FGF family act on many cell types of different function and embryologic origin.

The inventors herein have identified that FGF-20 is expressed in the brain, but not in other adult tissues, including heart, lung, liver, kidney and small intestine. This suggests a role for FGF-20 in, for example, Parkinson's disease and other diseases of neural tissue.

The present invention also includes therapeutic or pharmaceutical compositions comprising FGF-20 in an effective amount for treating patients with neuronal disease including Parkinson's disease, and a method comprising administering a therapeutically effective amount of FGF-20. These compositions and methods are useful for treating a number of diseases. The compositions and methods herein can also be useful to prevent degeneration and/or promote survival in other non-neuronal tissues as well. One skilled in the art can readily use a variety of assays known in the art to determine whether FGF-20 would be useful in promoting survival or functioning in a particular cell type, such as neuronal cells.

In certain circumstances, it may be desirable to modulate or decrease the amount of FGF-20 expressed. Thus, in another aspect of the present invention, FGF-20 anti-sense oligonucleotides can be made and a method utilized for diminishing the level of expression of FGF-20 by a cell comprising administering one or more FGF-20 anti-sense oligonucleotides. By FGF-20 anti-sense oligonucleotides reference is made to oligonucleotides that have a nucleotide sequence that interacts through base pairing with a specific complementary nucleic acid sequence involved in the expression of FGF-20 such that the expression of FGF-20 is reduced. Preferably, the specific nucleic acid sequence involved in the expression of FGF-20 is a genomic DNA molecule or mRNA molecule that encodes FGF-20. This genomic DNA molecule can comprise regulatory regions of the FGF-20 gene, or the coding sequence for mature FGF-20 protein. The term complementary to a nucleotide sequence in the context of FGF-20 antisense oligonucleotides and methods therefor means sufficiently complementary to such a sequence as to allow hybridization to that sequence in a cell, i.e., under physiological conditions. The FGF-20 antisense oligonucleotides preferably comprise a sequence containing from about 8 to about 100 nucleotides and more preferably the FGF-20 antisense oligonucleotides comprise from about 15 to about 30 nucleotides. The FGF-20 antisense oligonucleotides can also contain a variety of modifications that confer resistance to nucleolytic degradation such as, for example, modified internucleoside linages (Uhlmann and Peyman, *Chemical Reviews* 90:543–548 1990; Schneider and Banner, *Tetrahedron Lett.* 31:335 (1990), which are incorporated by reference), modified nucleic acid bases and/or sugars and the like.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation. For treating tissues in the central nervous system, administration can be by injection or infusion into the cerebrospinal fluid (CSF). When it is intended that FGF-20 be administered to cells in the central nervous system, administration can be with one or more agents capable of promoting penetration of FGF-20 across the blood-brain barrier.

FGF-20 can also be linked or conjugated with agents that provide desirable pharmaceutical or pharmacodynamnic properties. For example, FGF-20 can be coupled to any substance known in the art to promote penetration or transport across the blood-brain barrier such as an antibody to the transferrin receptor, and administered by, intravenous injection (see, for example, Friden et al., *Science* 259:373–377 (1993), which is incorporated by reference). Furthermore, FGF-20 can be stably linked to a polymer such as polyethylene glycol to obtain desirable properties of solubility, stability, half-life and other pharmaceutically advantageous properties. (See, for example, Davis et al., *Enzyme Eng.* 4:169–73 (1978); Burnham, *Am. J. Hosp. Pharm.* 51:210–218 (1994), which are incorporated by reference.)

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. FGF-20 can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing FGF-20 are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

Depending on the treatment regimen contemplated, it may be desired to control the rate of release of FGF-20 protein or variant thereof to provide long-term treatment while minimizing the frequency of administration. Such treatment regimens may be desired, for example, where the FGF-20 protein is found to be relatively unstable such that the localized concentration of active protein is at an efficacious level for an insufficient period of time. Thus, for example, for certain diseases, it may not be desired or practical to perform repeated and frequent injections. The major advantages of such sustained release systems include targeted local delivery of drugs at a constant rate, less drug required to treat the disease state, minimization of possible side effects, and enhanced efficacy of treatment. Also, these forms of delivery systems are capable of protecting drugs that are unstable in vivo and that would normally require a frequent dosing interval. Under such circumstances, sustained release may be achieved by one of the methods readily available in the art such as the encapsulation of FGF-20 conjugated heparin-Sepharose beads to form heparin-alginate microspheres or the preparation of FGF-20 PLG microspheres.

Heparin-alginate microspheres have been successfully employed for the delivery of Basic Fibroblast Growth Factor to tissue (Lopez et al., *Journal of Pharmacology and Experimental Therapeutics* 282(1):385–390 (1997)). Similarly, Alginate/heparin-Sepharose microspheres and films have been used as drug carriers to control the release of a basic FGF-saponin conjugate in order to control its release in small doses. Addition of heparin to solutions of bFGF prevents losses in activity that accompany changes in pH. or elevation in temperature. See, for example, Gospodarowicz et al., *J. Cell. Physiol.* 128:475–484 (1986).

As disclosed herein, FGF-20 has a heparin binding domain at residues 170–186. Accordingly, binding of FGF-20 to heparin may be employed in order to enhance its stability either during in vivo expression or administration or in vitro during various stages of protein purification. Thus, by the present invention, heparin may be added to a solution of FGF-20 and the activity assayed by the methods disclosed herein. FGF-20 bound heparin-Sepharose beads may be encapsulated into calcium alginate microspheres to permit the controlled release of the heparin-stabilized FGF-20 protein. For example, microspheres may be constructed by dropping a mixed solution of sodium alginate with FGF-20 bound heparin-Sepharose beads into a hardening solution of calcium chloride. Spheres are formed instantaneously as the mixture enters the hardening solution. The size of the microsphere may be adjusted by passing the FGF-20 bound heparin-Sepharose beads through a cylinder of reduced cross-sectional area such as through a hypodermic needle.

Encapsulation efficiency may be determined by comparing the amount of encapsulated growth factor with that initially present in solution. For example, the FGF-20 may be stripped from the heparin-Sepharose beads with a solution of 3 M NaCl and functional activity assays may be performed.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, FGF-20 may be therapeutically administered by implanting into patients vectors or cells capable of producing a biologically-active form of FGF-20 or a precursor of FGF-20, i.e., a molecule that can be readily converted to a biological-active form of FGF-20 by the body. In one approach cells that secrete FGF-20 may be encapsulated into semipermeable membranes for implantation into a patient. The cells can be cells that normally express FGF-20 or a precursor thereof or the cells can be transformed to express FGF-20 or a precursor thereof. It is preferred that the cell be of human origin and that the FGF-20 be human FGF-20 when the patient is human. However, the formulations and methods herein can be used for veterinary as well as human applications and the term "patient" as used herein is intended to include human and veterinary patients.

Cells can be grown ex vivo for use in transplantation or engraftment into patients (Muench et al., *Leuk & Lymph.* 16:1–11 (1994), which is incorporated by reference). In another embodiment of the present invention, FGF-20 is used to promote the ex vivo expansion of a cells for transplantation or engraftment. Current methods have used bioreactor culture systems containing factors such as erythropoietin, colony stimulating factors, stem cell factor, and interleukins to expand hematopoietic progenitor cells for erythrocytes, monocytes, neutrophils, and lymphocytes (Verfaillie, *Stem Cells* 12:466–476 (1994), which is incorporated by reference). These stem cells can be isolated from the marrow of human donors, from human peripheral blood, or from umbilical cord blood cells. The expanded blood cells are used to treat patients who lack these cells as a result of specific disease conditions or as a result of high dose chemotherapy for treatment of malignancy (George, *Stem Cells* 12(Suppl 1):249–255 (1994), which is incorporated by reference). In the case of cell transplant after chemotherapy, autologous transplants can be performed by removing bone marrow cells before chemotherapy, expanding the cells ex vivo using methods that also function to purge malignant cells, and transplanting the expanded cells back into the patient following chemotherapy (for review, see Rummel and Van Zant, *J. Hematotherapy* 3:213–218 (1994), which is incorporated by reference). Since FGF-20 is expressed in neural cells, it is believed that FGF-20 can function to prevent or slow the degeneration of dopaminergic neurons, such as substantia nigra.

In a number of circumstances it would be desirable to determine the levels of FGF-20 in a patient. The identification of FGF-20 along with the data herein showing expression of FGF-20 provides the basis for the conclusion that the presence of FGF-20 serves a normal physiological function related to cell growth and survival. Indeed, other neurotrophic factors are known to play a role in the function of neuronal and non-neuronal tissues. (Scully and Otten, *Cell Bol. Int.* 19:459–469 (1995); Otten and Gadient, *Int. J. Devl. Neurosciences* 13:147–151 (1995), which are incorporated by reference.) Endogenously produced FGF-20 may also play a role in certain disease conditions, particularly where there is cellular degeneration such as in neurodegenerative conditions or diseases. Other neurotrophic factors are known to change during disease conditions. For example, in multiple sclerosis, levels of NGF protein in the cerebrospinal fluid are increased during acute phases of the disease (Bracci-Laudiero et al., *Neuroscience Lett.* 147:9–12 (1992), which is incorporated by reference) and in systemic lupus erythematosus there is a correlation between inflammatory episodes and NGF levels in sera (Bracci-Laudiero et al., *Neuro Report* 4:563–565 (1993), which is incorporated by reference).

Given that FGF-20 is expressed in adult neural cells and in cochlear cells during embryonic development, it is likely that the level of FGF-20 may be altered in a variety of conditions and that quantification of FGF-20 levels would provide clinically useful information. Furthermore, in the treatment of degenerative conditions, compositions containing FGF-20 can be administered and it would likely be desirable to achieve certain target levels of FGF-20 in sera, in cerebrospinal fluid or in any desired tissue compartment. It would, therefore, be advantageous to be able to monitor the levels of FGF-20 in a patient. Accordingly, the present invention also provides methods for detecting the presence of FGF-20 in a sample from a patient.

The term "detection" as used herein in the context of detecting the presence of FGF-20 in a patient is intended to include the determining of the amount of FGF-20 or the ability to express an amount of FGF-20 in a patient, the distinguishing of FGF-20 from other growth factors, the estimation of prognosis in terms of probable outcome of a degenerative disease and prospect for recovery, the monitoring of the FGF-20 levels over a period of time as a measure of status of the condition, and the monitoring of FGF-20 levels for determining a preferred therapeutic regimen for the patient.

To detect the presence of FGF-20 in a patient, a sample is obtained from the patient. The sample can be a tissue biopsy sample or a sample of blood, plasma, serum, CSF or the like. FGF-20 is expressed in neural tissues as discussed in Example 8. Samples for detecting FGF-20 can be taken from this tissue. When assessing peripheral levels of FGF-20, it is preferred that the sample be a sample of blood, plasma or serum. When assessing the levels of FGF-20 in the central nervous system a preferred sample is a sample obtained from cerebrospinal fluid or neural tissue.

In some instances it is desirable to determine whether the FGF-20 gene is intact in the patient or in a tissue or cell line within the patient. By an intact FGF-20 gene it is meant that there are no alterations in the gene such as point mutations, deletions, insertions, chromosomal breakage, chromosomal rearrangements and the like wherein such alteration might alter production of FGF-20 or alter its biological activity, stability or the like to lead to disease processes or susceptibility to cellular degenerative conditions. Thus, in one embodiment of the present invention a method is provided for detecting and characterizing any alterations in the FGF-20 gene. The method comprises providing an oligonucleotide that contains the FGF-20 cDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize to the FGF-20 gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact FGF-20 gene or an FGF-20 gene abnormality.

Hybridization to an FGF-20 gene would involve denaturing the chromosomal DNA to obtain a single-stranded DNA; contacting the single-stranded DNA with a gene probe associated with the FGF-20 gene sequence; and identifying the hybridized DNA-probe to detect chromosomal DNA containing at least a portion of a human FGF-20 gene.

The term "probe" as used herein refers to a structure comprised of a polynucleotide that forms a hybrid structure with a target sequence, due to complementarity of probe sequence with a sequence in the target region. Oligomers suitable for use as probes may contain a minimum of about 8–12 contiguous nucleotides which are complementary to the targeted sequence and preferably a minimum of about 20.

The FGF-20 gene probes of the present invention can be DNA or RNA oligonucleotides and can be made by any method known in the art such as, for example, excision, transcription or chemical synthesis. Probes may be labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25°–45° C., more preferably at 32°–40° C. and more preferably at 37°–38° C. the time reguired for hybridization is from about 0.25 to about 96 hours, more preferably from about one to about 72 hours, and most preferably from about 4 to about 24 hours.

FGF-20 gene abnormalities can also be detected by using the PCR method and primers that flank or lie within the FGF-20 gene. The PCR method is well known in the art. Briefly, this method is performed using two oligonucleotide primers which are capable of hybridizing to the nucleic acid sequences flanking a target sequence that lies within an FGF-20 gene and amplifying the target sequence. The terms "oligonucleotide primer" as used herein refers to a short strand of DNA or RNA ranging in length from about 8 to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, a method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising FGF-20 or pre-pro FGF-20 or a fragment thereof is then directly sequenced and analyzed by comparison of the sequence with the sequences disclosed herein to identify alterations which might change activity or expression levels or the like.

In another embodiment, a method for detecting FGF-20 is provided based upon an analysis of tissue expressing the FGF-20 gene, as described in the Examples. The method comprises hybridizing a polynucleotide to mRNA from a sample of tissue that normally expresses the FGF-20 gene. The sample is obtained from a patient suspected of having an abnormality in the FGF-20 gene or in the FGF-20 gene of particular cells.

To detect the presence of mRNA encoding FGF-20 protein, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques.

The mRNA of the sample is contacted with a DNA sequence serving as a probe to form hybrid duplexes. The use of a labeled probes as discussed above allows detection of the resulting duplex.

When using the cDNA encoding FGF-20 protein or a derivative of the cDNA as a probe, high stringency conditions can be used in order to prevent false positives, that is the hybridization and apparent detection of FGF-20 nucleotide sequences when in fact an intact and functioning FGF-20 gene is not present. When using sequences derived from the FGF-20 cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide.

In order to increase the sensitivity of the detection in a sample of mRNA encoding the FGF-20 protein, the technique of reverse transcription/polymerization chain reaction (RT/PCR) can be used to amplify cDNA transcribed from mRNA encoding the FGF-20 protein. The method of RT/PCR is well known in the art, and can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and FGF-20 specific primers. (Belyavsky et al., *Nucl. Acid Res.* 17:2919–2932 (1989); Krug and Berger, *Methods in Enzymology* 152:316–325, Academic Press, New York, 1987, which are incorporated by reference).

The polymerase chain reaction method is performed as described above using two oligonucleotide primers that are substantially complementary to the two flanking regions of the DNA segment to be amplified.

Following amplification, the PCR product is then electrophoresed and detected by ethidium bromide staining or by phosphoimaging.

The present invention further provides for methods to detect the presence of FGF-20 protein in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (For example, see *Basic and Clinical Immunology*, 217–262, Sites and Terr, eds., Appleton & Lange, Norwalk, Conn., 1991 which is incorporated by reference). Preferred are binder-ligand immunoassay methods including reacting antibodies with an epitope or epitopes of the FGF-20 protein and competitively displacing a labeled FGF-20 protein or derivative thereof. Preferred antibodies are prepared according to Example 11.

As used herein, a derivative of the FGF-20 protein is intended to-include a polypeptide in which certain amino acids have been deleted, replaced, or changed to modified or unusual amino acids wherein the FGF-20 derivative is biologically equivalent to FGF-20 and wherein the polypeptide derivative cross-reacts with antibodies raised against the FGF-20 protein. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to the FGF-20 protein or an epitope thereof can be made for use in immunoassays by any of a number of methods known in the art. By epitope reference is made to an antigenic determinant of a polypeptide. An epitope could comprise 3 amino acids in a spatial conformation which is unique to the epitope. Generally an epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse (see Example 11).

Oligopeptides can be selected as candidates for the production of an antibody to the FGF-20 protein based upon the oligopeptides lying in hydrophilic regions, which are thus likely to be exposed in the mature protein. Oligopeptides for raising antibodies include the contiguous amino acids at positions 176–189, or 56–70 of SEQ ID NO:4. These oligopeptides are RDGARSKRHQKFTH (SEQ ID NO:5) and QLAHLHGILRRRQLY (SEQ ID NO:6). Additional oligopeptides can be determined using, for example, the Antigenicity Index of Welling, G. W. et al., *FEBS Lett.* 188:215–218 (1985), incorporated herein by reference.

Antibodies to FGF-20 can also be raised against oligopeptides that include one or more of the conserved regions identified herein such that the antibody can cross-react with other family members. Such antibodies can be used to identify and isolate the other family members.

Methods for preparation of the FGF-20 protein or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J., Am. Chem. Soc.* 85:2149 (1963), which is incorporated by reference) or the FMOC strategy on a Rapid Automated Multiple Peptide Synthesis system (E.I. du Pont de Nemours Company, Wilmington, Del.) (Caprino and Han,*J. Org. Chem.* 37:3404 (1972), which is incorporated by reference).

Polyclonal antibodies can be prepared by immunizing rabbits or other animals by injecting antigen followed by subsequent boosts at appropriate intervals. The animals are bled and sera assayed against purified FGF-20 protein usually by ELISA or by bioassay based upon the ability to block the action of FGF-20 on neurons or other cells. When using avian species, eg., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells, (Milstein and Kohler, *Nature* 256:495–497 (1975); Gulfre and Milstein, *Methods in Enzymology: Immunochemical Techniques* 73:1–46, Langone and Banatis eds., Academic Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating an overexpression of the protein. Thus, another aspect of the present invention provides for a method for preventing or treating diseases involving overexpression of the FGF-20 protein by treatment of a patient with specific antibodies to the FGF-20 protein.

Specific antibodies, either polyclonal or monoclonal, to the FGF-20 protein can be produced by any suitable method known in the art as discussed above. For example, murine or human monoclonal antibodies can be produced by hybridoma technology or, alternatively, the FGF-20 protein, or an immunologically active fragment thereof, or an anti-idiotypic antibody, or fragment thereof can be administered to an animal to elicit the production of antibodies capable of recognizing and binding to the FGF-20 protein. Such antibodies can be from any class of antibodies including, but not limited to IgG, IgA, IgM, IgD, and IgE or in the case of avian species, IgY and from any subclass of antibodies.

Polypeptides encoded by the instant polynucleotides and corresponding full-length genes can be used to screen peptide libraries, protein libraries, small molecule libraries, and phage display libraries, and other known methods, to identify analogs or antagonists.

Native FGF polypeptides may play a role in cancer. For example, FGF family members can induce marked morphological transformation of NIH 3T3 cells, and exhibit strong tumorigenicity in nude mice. Angiogenic activity has been exhibited by FGF family members. Thus, inhibitors of FGF can be used to treat cancer.

A library of peptides may be synthesized following the methods disclosed in U.S. Pat. No. 5,010,175, and in PCT No. WO 91/17823. As described below in brief, a mixture of peptides is prepared, which is then screened to identify the peptides exhibiting the desired signal transduction and receptor binding activity. According to the method of the '175 patent, a suitable peptide synthesis support (e.g., a resin) is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length (e.g., hexamers) is formed. Note that one need not include all amino acids in each step: one may include only one or two amino acids in some steps (e.g., where it is known that a particular amino acid is essential in a given position), thus reducing the complexity of the mixture. After the synthesis of the peptide library is completed, the mixture of peptides is screened for binding to the selected polypeptide. The peptides are then tested for their ability to inhibit or enhance activity. Peptides exhibiting the desired activity are then isolated and sequenced.

The method described in PCT No. WO 91/17823 is similar. However, instead of reacting the synthesis resin with a mixture of activated amino acids, the resin is divided into twenty equal portions (or into a number of portions corresponding to the number of different amino acids to be added in that step), and each amino acid is coupled individually to its portion of resin. The resin portions are then combined, mixed, and again divided into a number of equal portions for reaction with the second amino acid. In this manner, each reaction may be easily driven to completion. Additionally, one may maintain separate "subpools" by treating portions in parallel, rather than combining all resins at each step. This simplifies the process of determining which peptides are responsible for any observed receptor binding or signal transduction activity.

In such cases, the subpools containing, e.g., 1–2,000 candidates each are exposed to one or more polypeptides of the invention. Each subpool that produces a positive result is then resynthesized as a group of smaller subpools (sub-subpools) containing, e.g., 20–100 candidates, and reassayed. Positive sub-subpools may be resynthesized as individual compounds, and assayed finally to determine the peptides that exhibit a high binding constant. These peptides can be tested for their ability to inhibit or enhance the native activity. The methods described in PCT No. WO 91/7823 and U.S. Pat. No. 5,194,392 (herein incorporated by reference) enable the preparation of such pools and subpools by automated techniques in parallel, such that all synthesis and resynthesis may be performed in a matter of days.

Peptide agonists or antagonists are screened using any available method, such as signal transduction, antibody binding, receptor binding and mitogenic assays. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide may require concentrations equal to or greater than the native concentration, while inhibitors capable of binding irreversibly to the polypeptide may be added in concentrations on the order of the native concentration.

The availability of hFGF-20 and rFGF-20 allows for the identification of small molecules and low molecular weight compounds that inhibit the binding of FGF-20 to its receptor, through routine application of high-throughput screening methods (HTS). HTS methods generally refer to technologies that permit the rapid assaying of lead compounds for therapeutic potential. HTS techniques employ robotic handling of test materials, detection of positive signals, and interpretation of data. Lead compounds may be identified via the incorporation of radioactivity or through optical assays that rely on absorbance, fluorescence or luminescence as read-outs. Gonzalez, J. E., et al., *Curr. Opin. Biotech.* 9:624–631 (1998). Assays for detecting interaction between an FGF molecule and FGF receptor are described in, for example, Blunt, A. G. et al., *J. Biol. Chem.* 272:3733–3738 (1997), and such assays can be adapted for determining if a candidate molecule can inhibit the interaction between FGF-20 and its receptor.

Model systems are available that can be adapted for use in high throughput screening for compounds that inhibit the interaction of FGF-20 with receptors to which it binds (see Example 12), for example by competing with FGF-20 for receptor binding. Sarubbi et al., *Anal. Biochem.* 237:70–75 (1996), describe cell-free, non-isotopic assays for discovering molecules that compete with natural ligands for binding to the active site of IL-1 receptor. Martens, C. et al., *Anal. Biochem.* 273:20–31 (1999), describe a generic particle-based nonradioactive method in which a labeled ligand binds to its receptor immobilized on a particle; label on the particle decreases in the presence of a molecule that competes with the labeled ligand for receptor binding.

The therapeutic FGF-20 polynucleotides and polypeptides of the present invention may be utilized in gene delivery vehicles. The gene delivery vehicle may be of viral or non-viral origin (see generally, Jolly, *Cancer Gene Therapy* 1:51–64 (1994); Kimura, *Human Gene Therapy* 5:845–852 (1994); Connelly, *Human Gene Therapy* 1:185–193 (1995); and Kaplitt, *Nature Genetics* 6:148–153 (1994)). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 73 1; WO 90/07936; WO 94/03622; WO 93/25698; WO 93/25234; U.S. Pat. No. 5,219,740; WO 93/11230; WO 93/10218; Vile and Hart, *Cancer Res.* 53:3860–3864 (1993); Vile and Hart, *Cancer Res.* 53:962–967 (1993); Ram et al., *Cancer Res.* 53:83–88 (1993); Takamiya et al., *J. Neurosci. Res.* 33:493–503 (1992); Baba et al., *J. Neurosurg.* 79:729–735 (1993); U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., *J. Vir.* 63:3822–3828 (1989); Mendelson et al., *Virol.* 166:154–165 (1988); and Flotte et al., *P.N.A.S.* 90:10613–10617 (1993).

AAV vectors may be suitable for administering FGF-20 to treat hearing disorders. For example, Lalwani et al., *Gene Ther.* 3:588–592 (1996), used AAV to obtain in vivo expression of a foreign gene in the cochlea of guinea pigs.

Representative examples of adenoviral vectors include those described by Berkner, *Biotechniques* 6:616–627 (*Biotechniques*); Rosenfeld et al., *Science* 252:431–434 (1991); WO 93/19191; Kolls et al., *P.N.A.S.* :215–219 (1994); Kass-Eisler et al., *P.N.A.S.* 90:11498–11502 (1993); Guzman et al., *Circulation* 88:2838–2848 (1993); Guzman et al., *Cir. Res.* 73:1202–1207 (1993); Zabner et al., *Cell* 75:207–216 (1993); Li et al., *Hum. Gene Ther.* 4:403–409 (1993); Cailaud et al., *Eur. J. Neurosci.* 5:1287–1291 (1993); Vincent et al., *Nat. Genet.* 5:130–134 (1993); Jaffe et al., *Nat. Genet.* 1:372–378 (1992); and Levrero et al., *Gene* 101:195–202 (1992). Exemplary adenoviral gene therapy vectors employable in this invention also include those described in WO 94/12649, WO 93/03769; WO 93/19191; WO 94/28938; WO 95/11984 and WO 95/00655. Administration of DNA,linked to killed adenovirus as described in Curiel, *Hum. Gene Ther.* 3:147–154 (1992), may be employed.

Other gene delivery vehicles and methods may be employed, including polycationic condensed DNA linked or unlinked to killed adenovirus alone, for example Curiel, *Hum. Gene Ther.* 3:147–154 (1992); ligand-linked DNA, for example see Wu, *J. Biol. Chem.* 264:16985–16987 (1989); eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Biol.* 14:2411–2418 (1994), and in Woffendin, *Proc. Natl. Acad. Sci.* 91:1581–1585 (1994).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Patent Publication Nos. WO 95/13796, WO 94/23697, and WO 91/14445, and EP No. 0 524 968.

Further non-viral delivery suitable for use includes mechanical delivery systems such as the approach described in Woffendin et al., *Proc. Natl. Acad. Sci. USA* 91(24):1 1581–11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033.

FGF has been implicated in diseases characterized by loss of function, inadequate function/number, abnormal function or death of cells, tissues or organs for which function or survival can be prolonged/rescued, and abnormalities reversed or prevented by therapy with FGF.

Loss of pulmonary, bronchia or alveolar cells or function, healing of pulmonary or bronchia wounds, pulmonary infraction, emphysema/chronic obstructive pulmonary disease, asthma, sequelae of infectious or autoimmune disease, sequelae of pulmonary arterial or venous hypertension, pulmonary fibrosis, pulmonary disease of immaturity, and cystic fibrosis are conditions amenable to treatment with FGF.

Ischemic vascular disease may be amenable to FGF-20 treatment, wherein the disease is characterized by inadequate blood flow to an organ(s). Treatment may induce therapeutic angiogenesis or preserve function/survival of cells (myocardial ischemia/infarction, peripheral vascular disease, renal artery disease, stroke). Cardiomyopathies characterized by loss of function or death of cardiac myocytes or supporting cells in the heart (congestive heart failure, myocarditis) may also be treated using FGF-20, as can musculoskeletal disease characterized by loss of function, inadequate function or death of skeletal muscle cells, bone cells or supporting cells. Examples include skeletal myopathies, bone disease, and arthritis.

FGF-20 polynucleotides and polypeptides may aid in correction of congenital defects due to loss of FGF-20 molecule or its function (heart, lung, brain, limbs, kidney, etc.). FGF-20 polynucleotides and polypeptides may also aid in the correction of such defects wherein the defects lead to hearing loss due to cochlear defects.

Treatment of wound healing is yet another use of FGF-20 polypeptides and polynucleotides, either due to trauma, disease, medical or surgical treatment, including regeneration of cell populations and tissues depleted by these processes. Examples include liver regeneration, operative wound healing, re-endothelialization of injured blood vessels, healing of traumatic wounds, healing of ulcers due to vascular, metabolic disease, etc., bone fractures, loss of cells due to inflammatory disease, etc.

FGF-20 may also be used in screens to identify drugs for treatment of cancers which involve over activity of the molecule, or new targets which would be useful in the identification of new drugs.

For all of the preceding embodiments, the clinician will determine, based on the specific condition, whether FGF-20 polypeptides or polynucleotides, antibodies to FGF-20, or small molecules such as peptide analogues or antagonists, will be the most suitable form of treatment. These forms are all within the scope of the invention.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

Example 1

Preparation of RNA—RNA was prepared from adult rat brain using an RNA extraction kit (Pharmacia Biotech, Uppsala, Sweden). Poly (A)$^+$ RNA was prepared using pligo (dT)-cellulose (Type 2, Collaborative Biomedical Products, Bedford, Mass.).

Example 2

Isolation and Analysis of Rat FGF-20 cDNA—DNA was amplified from rat genomic DNA by polymerase chain reaction (PCR) for 30 cycles in 25 μl of a reaction mixture containing 5 pmole/μl of each of the sense and antisense degenerate primers representing all possible codons corresponding to the consensus amino acid sequences of rat FGF-9 (17) and FGF-16 (21), FEENWY (SEQ ID NO:10 and THFLPR (SEQ ID NO:11), respectively. The amplified product was further amplified by PCR with each of the sense and antisense degenerate primers representing all possible codons corresponding to another consensus amino acid sequences of rat FGF-9 (17) and FGF-16 (21), ENWYNT (SEQ ID NO:12) and HQKFTH (SEQ ID NO:13), respectively. The amplified DNA of expected size (approximately 150 base pairs) was cloned into the pGEM-T DNA vector (Promega, Madison, Wis.). The nucleotide sequence of the cloned DNA was determined by a DNA sequencer (Applied Biosystems, Foster, Calif.). To determine the coding region of a novel FGF cDNA, the coding region was amplified from cDNA synthesized from rat brain poly (A)$^+$ RNA by adaptor-ligation mediated polymerase chain reaction using a Marathon cDNA amplification kit (Clontech, Palo Alto, Calif.). To determine the amino-terminal region, DNA encoding the region was amplified from rat genomic DNA by cassette-ligation mediated polymerase chain reaction (Isegawa, Y. et al., *Mol. Cell. Probes* 6:467475 (1992)) using a LA PCR in vitro cloning kit (TaKaRa, Kyoto, Japan). The cDNA encoding the entire coding region of the FGF was amplified from rat brain cDNA by polymerase chain reaction in the presence of 5% dimethyl sulfoxide (Villarreal, X. C. et al., *Anal. Biochem.* 197:362–367 (1991)) using the FGF-specific primers including the 5' and 3' noncoding sequences, and cloned into the pGEM-T DNA vector. The apparent evolutionary relationships of members of the FGF family, were examined by the unweighted pair-group method with arithmetic mean method using the sequence analysis software, Genetyx (Software Development Co., Tokyo, Japan).

Example 3

Expression of FGF-20 mRNA in Rat Embryonic Inner Ears—Expression of FGF-20 in rat embryos was examined. Consecutive transverse sections of rat embryos (E14.5) were examined by in situ hybridization with $^{35}$S-labeled FGF-20 anti-sense and sense cRNA probes. The sections were counterstained with hematoxylin and eosin. Bright-field and dark-field photographs of the sections reveal that FGF-20 is preferentially expressed in the cochlea of the inner ear.

Example 4

Northern Blotting Analysis—Poly (A)hu + RNA (10 μg) from rat adult brain was dissolved on a denaturing agarose gel (1%) containing formaldehyde, and transferred to a nitrocellulose membrane in 20×SSC (1×SSC:0.15 M NACl/0.15 M sodium citrate) overnight. A $^{32}$P-labeled FGF-20 cDNA probe (~650 base pairs) was labeled with a random primer labeling kit (Pharmacia Biotech, Uppsala, Sweden) and deoxycytidine 5'-[α-$^{32}$P-] triphosphate (~1 10 TBq/mmol) (ICN Biomedicals Inc., Costa Mesa, Calif.). The membrane was incubated in hybridization solution containing the labeled probe as described (22), and analyzed with a radio-imaging analyzer (BAS 2000, Fuji Photo Film Co., Tokyo, Japan). To confirm the integrity of the poly (A)$^+$ RNA, the hybridized probe on the membrane was washed with 0.5×SSC containing 0.01 M EDTA (pH 8.0) at 100° C. mn for 5 min and with 0.05×SSC containing 0.01 M EDTA (pH 8.0) and 0.1% SDS at 60° C. for 15 min. The washed membrane was rehybridized with a $^{32}$P-labeled rat βactin cDNA probe (~410 base pairs) (Nudel, U. et al., *Nucleic Acids Res.* 11:1759–1771 (1983)).

Example 5

In Situ Hybridization—Adult Wistar rat brain was frozen in powdered dry ice, and sagittal sections were cut at 16 μm with a cryostat, thaw-mounted onto poly-L-lysine-coated slides, and stored at −85° C. until hybridization. A $^{35}$S-labeled rat FGF-20 antisense or sense cRNA probe was transcribed using SP6 RNA polymerase or T7 RNA polymerase (TaKaRa, Kyoto, Japan) with uridine 5'-α[$^{35}$S] thiotriphosphate (~30 TBq/mmol) (Amersham, Buckinghamshire, England), respectively. The sections were examined by in situ hybridization with the labeled probe as described (Yamasaki, M. et al., *J. Biol. Chem.* 271:15918–15921 (1996)).

Example 6

Preparation of Recombinant Rat FGF-20—The rat FGF-20 cDNA with a DNA fragment (75 BP) encoding an E-tag (GAPVPYPDPLEPR) (SEQ ID NO:14) and a His$_6$ tag (HHHHHH) (SEQ ID NO:15) at the 3'-terminus of the coding region was constructed in a transfer vector DNA, pBacPAK9 (Clontech, Palo Alto, Calif.). Recombinant baculovirus containing the FGF-20 cDNA with the tag sequences was obtained by cotransfection of Sf9 cells with the recombinant pBacPAK9 and a Bsu36 1-digested expression vector, BacPAK6 (Clontech, Palo Alto, Calif.). High Five insect cells were infected with the resultant recombinant baculovirus and incubated at 27° C. for 65 h in serum-free medium EX-CELL 400 (JRH Biosciences, Lenexa, Kans.). The culture medium was dialyzed against phosphate-buffered saline (PBS), and applied to a column of Ni-NTA agarose (QIAGEN GmbH, Hilden, Germany) in PBS containing 20 mM imidazole and 0.5 M NaCl. After washing the column with PBS containing 20 mM imidazole and 0.5 M NaCl, recombinant FGF-20 was eluted from the column with PBS containing 250 mM imidazole and 0.5 M NaCl, and applied to a column of Bio-Gel P-6 DG (Bio-Rad Lab., Hercules, Calif.) in PBS containing 100 μg/mlBSA.

Example 7

Detection of Recombinant FGF-20 by Western Blotting Analysis—The culture medium or rat recombinant FGF-20 was separated by sodium dodecyl sulfate (SDS)-polyacrylamide gel (12.5%) electrophoresis under reducing conditions and transferred onto a nitrocellulose membrane (Hybond-ECL, Amersharm, Buckinghamshire, England). The membrane was incubated with anti-E tag antibodies (1:500) (Pharmacia Biotech, Uppsala, Sweden). The protein with the E-tag was visualized as described (Hoshikawa, M. et al., *Biochem. Biophys. Res. Commun.* 244:187–191 (1998)).

Example 8

Rat Midbrain Cultured Cells—The ventral mesencephalon was resected from rat embryos (E16.5). The mesencephalic blocks were washed 10 times with Hanks' solution and mechanically dissociated without enzymatic treatment. The midbrain cultured cells were prepared essentially as described (Sawada, H. et al., *J. Neurosci. Res.* 43:503–510 (1996)). The culture medium consisted of Eagle's minimum essential medium (EMEM) supplemented with 0.2% sodium carbonate, 0.1% glucose, 0.029% L-glutamine and 0.238% HEPES. The cultured cells were incubated at 37° C. in the culture medium containing 10% fetal calf serum. From the $_5$h day of culture, the cells were incubated in 10 the culture medium containing 10% horse serum.

Example 9

Examination of Neurotrophic Activity of FGF-20 for Midbrain Dopaminergic Neurons—Cells on the 8$^{th}$ day of culture were incubated in Eagle's minimum essential medium supplemented with 0.2% sodium hydrogen carbonate, 0.1% glucose, 0.029% L-glutamine, 0.238% HEPES and 10% horse serum or 0.1% bovine serum albumin in the presence or absence of FGF-20 for 4 days and then fixed with fresh 4% paraformaldehyde for 30 min on the 12$^{th}$ day. Cells on the $_8$th day of culture were also incubated in the presence or absence of recombinant rat FGF-20 for 24 h and then were treated with 1 mM glutamate for 10 min. The cultured cells were further incubated in medium without FGF-20 and 1 mM glutamate and then fixed with 4% paraformaldehyde for 30 min on the 12$^{th}$ day. The fixed cells were washed with PBS for 15 min, and then treated with 0.2% Triton X-10 for 30 min. The cells were immunostained with anti-tyrosine hydroxylase (TH) antibody (Eugene Tech, Ridgefield Park, N.J.) essentially as described (Sawada, H. et al., *J. Neurosci. Res.* 43:503–510 (1996)). Numbers of cultured dopaninergic neurons were evaluated by counting cells stained with anti-TH antibody.

Example 10

Isolation and Analysis of Human FGF-20—The coding region of human FGF-20 DNA was amplified from human brain cDNA library (λgt10) by PCR using primers specific for FGF-20 and λgt10 DNA. The nucleotide sequence of the cDNA encoding the carboxy-terminal 112 amino acids of human FGF-20 was determined, and is shown in FIG. 7. An alignment of rat and human FGF-20 amino acid sequences is shown in FIG. 8.

Example 11

Preparation of Antisera to FGF-20 by Immunization of Rabbits with an FGF-20 Peptide—A peptide sequence corresponding to selected contiguous amino acids of the human FGF-20 protein is synthesized and coupled to keyhole limpet hemocyanin (KLH) as described (Harlow and Land, Antibodies: A Laboratory Manual, 1988. Cold Spring Harbor Laboratory, New York, N.Y.). The KLH-coupled peptide is used to immunize rabbits. Antisera are tested for specificity to FGF-20, and for cross-reactivity with other FGF proteins.

Exemplary peptide sequences are:
1. RDGARSKRHQKFTH (SEQ ID NO:5)
2. QLAHLHGILRRRQLY (SEQ ID NO:6)

Example 12

Binding of FGF-20 to the Recombinant Extracellular Domains of FGFR-1c, FGFR-2c, and FGFR-3c—Recombinant FGF-20 was fixed on the sensor tip CM5 (Amersham Pharmacia Biotech). Binding of the recombinant extracellular domain of FGFR-1c, FGFR-2c, or FGFR-3c to FGF-20 on the tip was analyzed using the BIACORE 2000 System (Amersham Pharmacia Biotech). The equilibrium dissociation constant was determined by the BIA evaluation software (Amersham Pharmacia Biotech).

TABLE I

Binding of FGF-20 to FGF Receptors

| Receptor | $K_{diss}$ (S$^{-1}$) | $K_{ass}$ (M$^{-1}$ · S$^{-1}$) | $K_d$ (M) |
|---|---|---|---|
| FGFR-1c | nd | nd | |
| FGFR-2c | $1.67 \times 10^{-2}$ | $5.95 \times 10^{5}$ | $2.81 \times 10^{-8}$ |
| FGFR-3c | $2.47 \times 10^{-2}$ | $1.15 \times 10^{5}$ | $2.17 \times 10^{-7}$ | nd not detected

As shown in Table 1, FGF-20 binds to FGF receptors 2 and 3, but not to FGF receptor 1. Thus, FGF-20 may exhibit biological effects not found in members of the FGF family that bind to FGF receptor 1, such as FGF-2 and FGF-4.

All patents, published patent applications and publications cited herein are incorporated by reference as if set forth fully herein.

Although certain preferred embodiments have been described herein, it is not intended that such embodiments be construed as limitations on the scope of the invention except as set forth in the following claims.

We claim:

1. A method of enhancing the survival of dopaminergic neurons in a patient in need thereof, the method comprising administering to the patient a composition comprising a polypeptide comprising the amino acid sequence of SEQ ID NO:4.

2. The method of claim 1 wherein the patient suffers from Parkinson's disease.

3. The method of claim 2 wherein the patient suffers from a condition affecting the substantia nigra.

4. A method of alleviating a disease condition in the brain of a human patient wherein said disease condition is alleviated by enhancing the survival of dopaminergic neurons in said human patient, said method comprising administering to said patient a pharmaceutically effective composition comprising a polypeptide having the amino acid sequence of SEQ ID NO:4.

* * * * *